US012806328B2

(12) United States Patent
Elder et al.

(10) Patent No.: US 12,806,328 B2
(45) Date of Patent: Nov. 24, 2026

(54) USER-FRIENDLY NEGATIVE PRESSURE WOUND THERAPY DEVICES AND METHODS OF OPERATING SUCH DEVICES

(71) Applicant: T.J.Smith and Nephew, Limited, Hull (GB)

(72) Inventors: David Michael Elder, Hull (GB); Pavel Ivan, Edinburgh (GB); Andrea Maggiore, Hull (GB); Christopher John Webb, South Ferriby (GB)

(73) Assignee: T.J.Smith and Nephew, Limited, Hull (GB)

( * ) Notice: Subject to any disclaimer, the term of this patent is extended or adjusted under 35 U.S.C. 154(b) by 306 days.

(21) Appl. No.: 18/701,812

(22) PCT Filed: Oct. 19, 2022

(86) PCT No.: PCT/EP2022/079091
§ 371 (c)(1),
(2) Date: Apr. 16, 2024

(87) PCT Pub. No.: WO2023/072704
PCT Pub. Date: May 4, 2023

(65) Prior Publication Data

US 2025/0025622 A1 Jan. 23, 2025

(30) Foreign Application Priority Data

Oct. 26, 2021 (GB) .................................... 2115353
Dec. 9, 2021 (GB) .................................... 2117771

(51) Int. Cl.
*A61M 1/00* (2006.01)

(52) U.S. Cl.
CPC .......... *A61M 1/98* (2021.05); *A61M 2205/33* (2013.01)

(58) Field of Classification Search
CPC ...... A61M 1/98; A61M 2205/33; A61M 1/96; A61M 1/966; A61M 1/985; A61M 1/982;
(Continued)

(56) References Cited

U.S. PATENT DOCUMENTS

2013/0172691 A1 7/2013 Tran
2016/0015871 A1 1/2016 Locke et al.
(Continued)

OTHER PUBLICATIONS

International Search Report and Written Opinion for Application No. PCT/EP2022/079091, mailed on May 4, 2023, 23 pages.
(Continued)

*Primary Examiner* — Susan S Su
*Assistant Examiner* — Erin A Kim
(74) *Attorney, Agent, or Firm* — Knobbe, Martens, Olson & Bear, LLP

(57) ABSTRACT

A negative pressure wound therapy device can be configured to monitor motion and determine that the device is falling as well as duration and height of the fall. Flat falls and rotating falls can be accurately detected. The device can provide an indication of the fall, including deactivating therapy. The device can monitor the amount exudate removed from a wound and determine whether transition to a low-exudate rate negative pressure wound therapy and suggest such transition. The device can utilize proportional-integral-derivative (PID) control loop to drive a negative pressure source of the device. The PID control loop can utilize different proportional gain and integral gain for different negative pressure setpoint to achieve target pressure quickly and without any large overshoots.

20 Claims, 20 Drawing Sheets

(58) Field of Classification Search
CPC ........ A61M 2205/18; A61M 2205/215; A61M 2205/3331; A61M 2205/3334; A61M 2205/3344; A61M 2205/3382; A61M 2205/3386; A61M 2205/3389; A61M 2205/3569; A61M 2205/702
See application file for complete search history.

(56) References Cited

U.S. PATENT DOCUMENTS

| | | | | |
|---|---|---|---|---|
| 2017/0188946 | A1 | 7/2017 | Klusmann et al. | |
| 2017/0209630 | A1 | 7/2017 | Klusmann et al. | |
| 2018/0177929 | A1 | 6/2018 | Adams et al. | |
| 2018/0250452 | A1* | 9/2018 | Locke | A61M 1/96 |
| 2021/0196869 | A1 | 7/2021 | Hartwell et al. | |
| 2022/0047799 | A1 | 2/2022 | Quintanar | |
| 2022/0096731 | A1 | 3/2022 | Seddon et al. | |

OTHER PUBLICATIONS

Invitation to Pay Additional Fees and Partial International Search Report for Application No. PCT/EP2022/079091, mailed on Feb. 2, 2023, 14 pages.
International Preliminary Report on Patentability for Application No. PCT/EP2022/079091, mailed on May 10, 2024, 14 pages.

* cited by examiner

USER-FRIENDLY NEGATIVE PRESSURE WOUND THERAPY DEVICES AND METHODS OF OPERATING SUCH DEVICES

CROSS-REFERENCE TO RELATED APPLICATIONS

This application is a U.S. national stage application of International Patent Application No. PCT/EP2022/079091, filed Oct. 19, 2022 and entitled "USER-FRIENDLY NEGATIVE PRESSURE WOUND THERAPY DEVICES AND METHODS OF OPERATING SUCH DEVICES," which claims priority to U.K. Provisional Application No. 2115353.1, filed Oct. 26, 2021 and entitled "USER-FRIENDLY NEGATIVE PRESSURE WOUND THERAPY DEVICES AND METHODS OF OPERATING SUCH DEVICES," and U.K. Provisional Application No. 2117771.2, filed Dec. 9, 2021 and entitled "USER-FRIENDLY NEGATIVE PRESSURE WOUND THERAPY DEVICES AND METHODS OF OPERATING SUCH DEVICES," the disclosure of each of which is hereby incorporated by reference in its entirety.

TECHNICAL FIELD

Embodiments described herein relate to apparatuses, systems, and methods for the treatment of wounds, for example using dressings in combination with negative pressure wound therapy.

DESCRIPTION OF THE RELATED ART

Many different types of wound dressings are known for aiding in the healing process of a human or animal. These different types of wound dressings include many different types of materials and layers, for example, gauze, pads, foam pads or multi-layer wound dressings. Topical negative pressure (TNP) therapy, sometimes referred to as vacuum assisted closure, negative pressure wound therapy, or reduced pressure wound therapy, is widely recognized as a beneficial mechanism for improving the healing rate of a wound. Such therapy is applicable to a broad range of wounds such as incisional wounds, open wounds, and abdominal wounds or the like. TNP therapy assists in the closure and healing of wounds by reducing tissue edema, encouraging blood flow, stimulating the formation of granulation tissue, removing excess exudates and may reduce bacterial load. Thus, reducing infection to the wound. Furthermore, TNP therapy permits less outside disturbance of the wound and promotes more rapid healing.

SUMMARY

A negative pressure wound therapy device can include a housing and a negative pressure source supported by the housing and configured to be connected, via a fluid flow path, to a wound covered by a wound dressing, the negative pressure source further configured to provide negative pressure to the wound. The device can include an electronic circuitry supported by the housing, the electronic circuitry configured to detect motion of the housing. The electronic circuitry can be configured to, based on the motion of the housing, detect that the housing is falling and determine a duration of the fall. The electronic circuitry can be configured to provide a first indication responsive to determining that the duration of the fall satisfies a duration threshold.

The negative pressure wound therapy device of any of the preceding paragraphs and/or any of the apparatuses, systems, or devices disclosed herein can include one or more of the following features. The electronic circuitry can include an accelerometer. The electronic circuitry can be configured to detect that the housing is falling responsive to determining that an acceleration detected by the accelerometer satisfies a first acceleration threshold indicative of low acceleration. Acceleration detected by the accelerometer can include or one or more of acceleration along a z-axis or a magnitude of acceleration along multiple axes. The electronic circuitry can be configured to determine the duration of the fall responsive to detecting a duration of time during which the acceleration detected by the accelerometer satisfies the first acceleration threshold. The electronic circuitry can be configured to determine a first time at which the acceleration detected by the accelerometer initially satisfies the first acceleration threshold. The electronic circuitry can be configured to determine a second time during which the housing make a first impact with a surface. The electronic circuitry can be configured to determine the duration of the fall based on a time difference between the second time and initial time, wherein determining the duration of the fall is based on the time difference accounts for a possible rotation of the housing during the fall. The electronic circuitry can be configured to determine the second time responsive to detecting that the acceleration detected by the accelerometer satisfies a second acceleration threshold indicative of high acceleration threshold.

The negative pressure wound therapy device of any of the preceding paragraphs and/or any of the apparatuses, systems, or devices disclosed herein can include one or more of the following features. The device can include an electronic processing circuitry configured to operate the negative pressure source. The electronic circuitry can be configured to cause the electronic processing circuitry to transition from a non-operational state to an operational state responsive to determining that the duration of the fall satisfies the duration threshold. The electronic circuitry can be configured to determine a height of the fall based on the duration of the fall. The first indication can include one or more of deactivating the negative pressure source or performing one or more tests of the device. The electronic circuitry can be configured to, based on the motion of the housing, detect that the housing is tilted and provide a second indication responsive to detecting that the housing is tilted. The electronic circuitry can include an accelerometer. The electronic circuitry can be configured to detect that the housing is tilted responsive to determining that an acceleration detected by the accelerometer satisfies a tilt threshold. Acceleration can be acceleration along the z-axis. The first indication can include deactivating the negative pressure source.

A negative pressure wound therapy device can include a negative pressure source configured to be connected, via a fluid flow path, to a wound covered by a wound dressing, the negative pressure source further configured to provide negative pressure to the wound. The device can include a canister configured to be fluidically connected to the negative pressure source via the fluid flow path and further configured to store fluid aspirated from the wound, the canister further configured to be disconnected from the negative pressure source and replaced by a replacement canister. The device can include an electronic processing circuitry configured to monitor a rate of aspiration of fluid from the wound based on monitoring replacement of the canister. The electronic circuitry can be configured to, responsive to determining that the rate of aspiration satisfies a threshold indicative of a transition to treating the wound with a low-exudate rate negative pressure wound therapy system, provide an indication that the transition is recommended.

The negative pressure wound therapy device of any of the preceding paragraphs and/or any of the apparatuses, systems, or devices disclosed herein can include one or more of the following features. The low-exudate rate negative pressure wound therapy system can be configured to store fluid aspirated from the wound in an absorbent dressing and does not utilize any canisters. The electronic processing circuitry can be configured to determine that the rate of aspiration satisfies the threshold responsive to detecting that at least one canister replacement occurred outside of a threshold time duration with the canister not being full. The threshold time duration can include three days. The at least one canister replacement can include two consecutive canister replacements. Sizes of the canister and replacement canister can include a first size and a second size larger than the first size. The electronic processing circuitry can be configured to determine that the rate of aspiration satisfies the threshold responsive to detecting that the canister is of the first size. The electronic processing circuitry can be configured to disregard the replacement canister from the monitoring replacement of the canister responsive to determining that the replacement canister has been previously used with a different negative pressure wound therapy device. The electronic processing circuitry can be configured to detect disconnecting the canister from being fluidically connected to the negative pressure source and subsequently reconnecting the canister and disregard reconnecting the canister from the monitoring replacement of the canister.

A negative pressure wound therapy device can include a negative pressure source configured to be connected, via a fluid flow path, to a wound covered by a wound dressing, the negative pressure source further configured to provide negative pressure to the wound. The device can include an electronic processing circuitry configured to operate the negative pressure source to establish a target negative pressure at the wound, the target negative pressure selected from a plurality of negative pressure set points. The electronic processing circuitry can be configured to control the negative pressure source using a proportional-integral-derivate (PID) control loop that uses a first pair of integral and proportional gains associated with a first negative pressure set point and a second pair of integral and proportional gains associated with a second negative pressure set point different from the first negative pressure set point, integral and proportional gains of the first pair different from integral and proportional gains of the second pair.

The negative pressure wound therapy device of any of the preceding paragraphs and/or any of the apparatuses, systems, or devices disclosed herein can include one or more of the following features. The PID control loop can use different pairs of integral and proportional gains for each negative pressure set point of the plurality of negative pressure set points. The electronic processing circuitry can be configured to increase integral gains of the first and second pairs responsive to determining that the target negative pressure has been reached. Proportional gains of the first and second pairs can be related to the first and second negative pressure set points by a linear or squared relationship.

A negative pressure wound therapy device can include a negative pressure source configured to be connected, via a fluid flow path, to a wound covered by a wound dressing, the negative pressure source further configured to provide negative pressure to the wound. The device can include an electronic processing circuitry configured to operate the negative pressure source to provide negative pressure to the wound. The device can include a canister positioned in the fluid flow path and configured to store fluid aspirated from the wound. The electronic processing circuitry can be configured to deactivate the negative pressure source responsive to detecting that the canister is full and a blockage is present in the fluid flow path.

The negative pressure wound therapy device of any of the preceding paragraphs and/or any of the apparatuses, systems, or devices disclosed herein can include one or more of the following features. The electronic processing circuitry can be configured to, subsequently to deactivating the negative pressure source, activate the negative pressure source responsive to at least one detecting that the canister is not full or blockage is not present in the fluid flow path.

Disclosed herein are methods of operating a negative pressure wound therapy device of any of the preceding paragraphs and/or any of the devices, apparatuses, or systems disclosed herein.

Disclosed herein are kits that include the negative pressure wound therapy device of any of the preceding paragraphs and/or any of the devices, apparatuses, or systems disclosed herein and one or more wound dressings.

Any of the features, components, or details of any of the arrangements or embodiments disclosed in this application, including without limitation any of the apparatus embodiments and any of the negative pressure wound therapy embodiments disclosed herein, are interchangeably combinable with any other features, components, or details of any of the arrangements or embodiments disclosed herein to form new arrangements and embodiments.

DETAILED DESCRIPTION

Figure 1A:
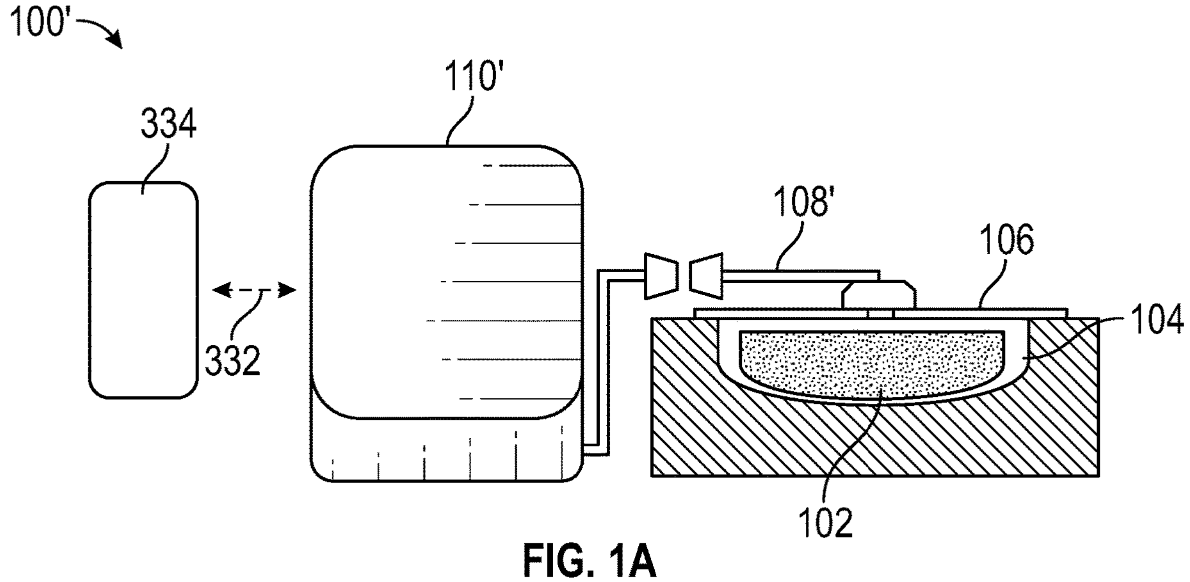
FIG. 1A illustrates a negative pressure wound therapy system.

Embodiments disclosed herein relate to systems and methods of treating and/or monitoring a wound. Some embodiments of the negative pressure wound therapy devices disclosed herein can include a negative pressure source configured to be connected and/or fluidically coupled, via a fluid flow path, to a wound covered by a wound dressing and provide negative pressure to a wound.

Throughout this specification reference is made to a wound. The term wound is to be broadly construed and encompasses open and closed wounds in which skin is torn, cut or punctured or where trauma causes a contusion, or any other superficial or other conditions or imperfections on the skin of a patient or otherwise that benefit from pressure treatment. A wound is thus broadly defined as any damaged region of tissue where fluid may or may not be produced. Examples of such wounds include, but are not limited to, abdominal wounds or other large or incisional wounds, either as a result of surgery, trauma, sterniotomies, fasciotomies, or other conditions, dehisced wounds, acute wounds, chronic wounds, subacute and dehisced wounds, traumatic wounds, flaps and skin grafts, lacerations, abrasions, contusions, burns, diabetic ulcers, pressure ulcers, stoma, surgical wounds, trauma and venous ulcers or the like.

Embodiments of systems and methods disclosed herein can be used with topical negative pressure ("TNP") or reduced pressure therapy systems. Briefly, negative pressure wound therapy assists in the closure and healing of many forms of "hard to heal" wounds by reducing tissue oedema, encouraging blood flow and granular tissue formation, or removing excess exudate and can reduce bacterial load (and thus infection risk). In addition, the therapy allows for less disturbance of a wound leading to more rapid healing. TNP therapy systems can also assist in the healing of surgically closed wounds by removing fluid. TNP therapy can help to stabilize the tissue in the apposed position of closure. A further beneficial use of TNP therapy can be found in grafts and flaps where removal of excess fluid is important and close proximity of the graft to tissue is required in order to ensure tissue viability.

As used herein, reduced or negative pressure levels, such as −X mmHg, represent pressure levels relative to normal ambient atmospheric pressure, which can correspond to 760 mmHg (or 1 atm, 29.93 inHg, 101.325 kPa, 14.696 psi, etc.). Accordingly, a negative pressure value of −X mmHg reflects pressure that is X mmHg below 760 mmHg or, in other words, a pressure of (760-X) mmHg. In addition, negative pressure that is "less" or "smaller" than X mmHg corresponds to pressure that is closer to atmospheric pressure (for example, −40 mmHg is less than −60 mmHg). Negative pressure that is "more" or "greater" than-X mmHg corresponds to pressure that is further from atmospheric pressure (for example, −80 mmHg is more than −60 mmHg). In some cases, local ambient atmospheric pressure is used as a reference point, and such local atmospheric pressure may not necessarily be, for example, 760 mmHg.

Systems and methods disclosed herein can be used with other types of treatment in addition to or instead of reduced pressure therapy, such as irrigation, ultrasound, heat or cold, neuro stimulation, or the like. In some cases, disclosed systems and methods can be used for wound monitoring without application of additional therapy. Systems and methods disclosed herein can be used in conjunction with a dressing, including with compression dressing, reduced pressure dressing, or the like.

A healthcare provider, such as a clinician, nurse, or the like, can provide a TNP prescription specifying, for example, the pressure level or time of application. However, the healing process is different for each patient and the prescription may affect the healing process in a way the clinician or healthcare provider did not expect at the time of devising the prescription. A healthcare provider may try to adjust the prescription as the wound heals (or does not heal), but such process may require various appointments that can be time consuming and repetitive. Embodiments disclosed herein provide systems, devices, or methods of efficiently adjusting TNP prescriptions and delivering effective TNP therapy.

Wound Therapy System

FIG. 1A schematically illustrates a negative pressure wound treatment system 100' (sometimes referred to as a reduced or negative pressure wound therapy system, a TNP system, or a wound treatment system). In any implementations disclosed herein, though not required, the negative pressure wound treatment system 100' can include a wound filler 102 placed on or inside a wound 104 (which may be a cavity). The wound 104 can be sealed by a wound cover 106, which can be a drape, such that the wound cover 106 can be in fluidic communication with the wound 104. The wound filler 102 in combination with the wound cover 106 can be referred to as a wound dressing. A tube or conduit 108' (also referred to herein as a flexible suction adapter or a fluidic connector) can be used to connect the wound cover 106 with a wound therapy device 110' (sometimes as a whole or partially referred to as a "pump assembly") configured to supply reduced or negative pressure. The conduit 108' can be a single or multi lumen tube. A connector can be used to removably and selectively couple a conduit or tube of the device 110' with the conduit 108'.

In any of the systems disclosed herein, a wound therapy device can be canisterless, wherein, for example and without limitation, wound exudate is collected in the wound dressing or is transferred via a conduit for collection at another location. However, any of the wound therapy devices disclosed herein can include or support a canister.

Additionally, with any of the wound therapy systems disclosed herein, any of the wound therapy devices can be mounted to or supported by the wound dressing or adjacent to the wound dressing. The wound filler 102 can be any suitable type, such as hydrophilic or hydrophobic foam, gauze, inflatable bag, and so on. The wound filler 102 can be conformable to the wound 104 such that the wound filler 102 substantially fills the cavity of the wound 104. The wound cover 106 can provide a substantially fluid impermeable seal over the wound 104. The wound cover 106 can have a top side and a bottom side. The bottom side can adhesively (or in any other suitable manner) seal with the wound 104, for example by sealing with the skin around the wound 104. The conduit 108 or any other conduit disclosed herein can be formed from polyurethane, PVC, nylon, polyethylene, silicone, or any other suitable material.

The wound cover 106 can have a port (not shown) configured to receive an end of the conduit 108. In some cases, the conduit 108 can otherwise pass through or under the wound cover 106 to supply reduced pressure to the wound 104 so as to maintain a desired level of reduced pressure in the wound 104. The conduit 108 can be any suitable article configured to provide at least a substantially sealed fluid flow pathway or path between the wound therapy device 110' and the wound cover 106, so as to supply the reduced pressure provided by the wound therapy device 110' to wound 104.

The wound cover 106 and the wound filler 102 can be provided as a single article or an integrated single unit. In some cases, no wound filler is provided and the wound cover by itself may be considered the wound dressing. The wound dressing can then be connected, via the conduit 108, to a source of negative pressure of the wound therapy device 110'. In some cases, though not required, the wound therapy device 110' can be miniaturized and portable, although larger conventional negative pressure sources (or pumps) can also be used.

The wound cover 106 can be located over a wound site to be treated. The wound cover 106 can form a substantially sealed cavity or enclosure over the wound. The wound cover 106 can have a film having a high water vapour permeability to enable the evaporation of surplus fluid, and can have a superabsorbing material contained therein to safely absorb wound exudate. In some cases, the components of the TNP systems described herein can be particularly suited for incisional wounds that exude a small amount of wound exudate.

The wound therapy device 110' can operate with or without the use of an exudate canister. In some cases, as is illustrated, the wound therapy device 110' can include an exudate canister. In some cases, configuring the wound therapy device 110' and conduit 108' so that the conduit 108' can be quickly and easily removed from the wound therapy device 110' can facilitate or improve the process of wound dressing or pump changes, if necessary. Any of the pump assemblies disclosed herein can have any suitable connection between the conduit 108' and the pump.

The wound therapy device 110' can deliver negative pressure of approximately −80 mmHg, or between about −20 mmHg and −200 mmHg. Note that these pressures are relative to normal ambient atmospheric pressure thus, −200 mmHg would be about 560 mmHg in practical terms. In some cases, the pressure range can be between about −40 mmHg and −150 mmHg. Alternatively, a pressure range of up to −75 mmHg, up to −80 mmHg or over −80 mmHg can be used. Also in some cases a pressure range of below −75 mmHg can be used. Alternatively, a pressure range of over approximately −100 mmHg, or even −150 mmHg, can be supplied by the wound therapy device 110'.

As will be described in greater detail below, the negative pressure wound treatment system 100' can be configured to provide a connection 332 to a separate or remote computing device 334. The connection 332 can be wired or wireless (such as, Bluetooth, Bluetooth low energy (BLE), Near-Field Communication (NFC), WiFi, or cellular). The remote computing device 334 can be a smartphone, a tablet, a laptop or another standalone computer, a server (such as, a cloud server), another pump device, or the like.

Figure 1B:
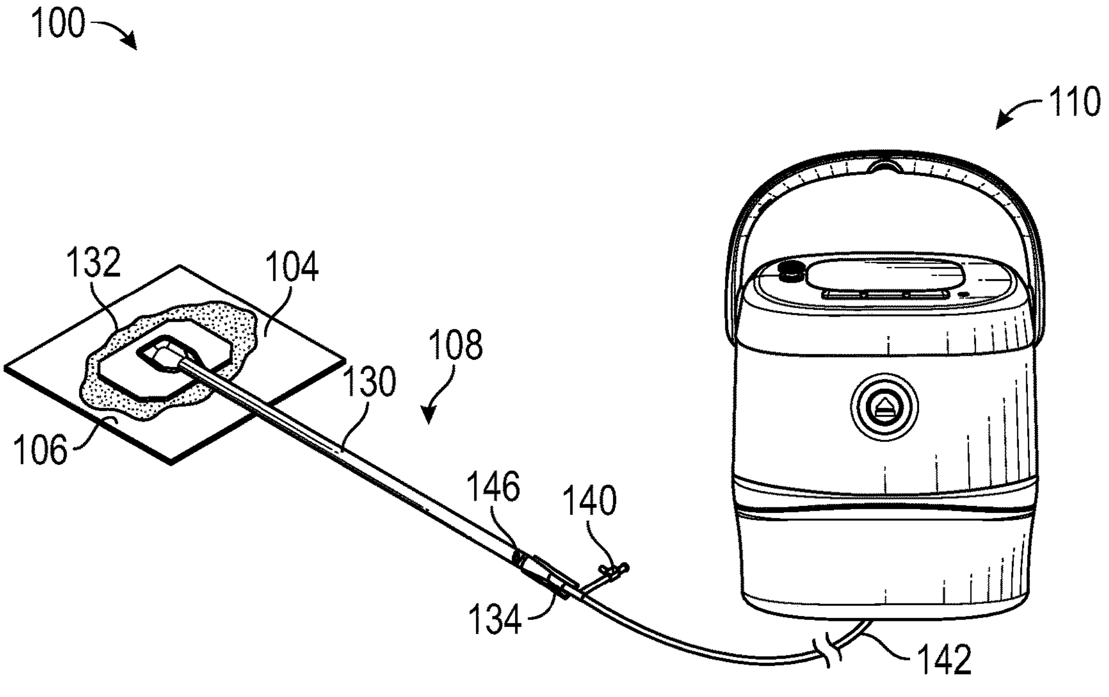
FIG. 1B illustrates another negative pressure wound therapy system.

FIG. 1B illustrates another negative pressure wound treatment system 100. The negative pressure wound treatment system 100 can have any of the components, features, or other details of any of the other negative pressure wound treatment system disclosed herein, including without limitation the negative pressure wound treatment system 100' illustrated in FIG. 1A or the negative pressure wound treatment system 400 illustrated in FIG. 4, in combination with or in place of any of the components, features, or other details of the negative pressure wound treatment system 100 shown in FIG. 1B and/or described herein. The negative pressure wound treatment system 100 can have a wound cover 106 over a wound 104 that can seal the wound 104. A conduit 108, such as a single or multi lumen tube can be used to connect the wound cover 106 with a wound therapy device 110 (sometimes as a whole or partially referred to as a "pump assembly") configured to supply reduced or negative pressure. The wound cover 106 can be in fluidic communication with the wound 104.

With reference to FIG. 1B, the conduit 108 can have a bridge portion 130 that can have a proximal end portion and a distal end portion (the distal end portion being closer to the wound 104 than the proximal end portion, and an applicator 132 at the distal end of the bridge portion 130 forming the flexible suction adapter (or conduit) 108. A connector 134 can be disposed at the proximal end of the bridge portion 130, so as to connect to at least one of the channels that can extend along a length of the bridge portion 130 of the conduit 108 shown in FIG. 1B. A cap 140 can be coupled with a portion of the conduit 108 and can, in some cases, as illustrated, be attached to the connector 134. The cap 140 can be useful in preventing fluids from leaking out of the proximal end of the bridge portion 130. The conduit 108 can be a Soft Port manufactured by Smith & Nephew. As mentioned, the negative pressure wound treatment system 100 can include a source of negative pressure, such as the device 110, capable of supplying negative pressure to the wound 104 through the conduit 108. Though not required, the device 110 can also include a canister or other container for the storage of wound exudates and other fluids that can be removed from the wound.

The device 110 can be connected to the connector 134 via a conduit or tube 142. In use, the applicator 132 can be placed over an aperture formed in a cover 106 that is placed over a suitably-prepared wound or wound 104. Subsequently, with the wound therapy device 110 connected via the tube 142 to the connector 134, the wound therapy device 110 can be activated to supply negative pressure to the wound. Application of negative pressure can be applied until a desired level of healing of the wound is achieved.

The bridge portion 130 can comprise an upper channel material or layer positioned between an upper layer and an intermediate layer, with a lower channel material or layer positioned between the intermediate layer and a bottom layer. The upper, intermediate, and lower layers can have elongate portions extending between proximal and distal ends and can include a material that is fluid-impermeable, for example polymers such as polyurethane. It will of course be appreciated that the upper, intermediate, and lower layers can each be constructed from different materials, including semi-permeable materials. In some cases, one or more of the upper, intermediate, and lower layers can be at least partially transparent. In some instances, the upper and lower layers can be curved, rounded or outwardly convex over a majority of their lengths.

The upper and lower channel layers can be elongate layers extending from the proximal end to the distal end of the bridge 130 and can each preferably comprise a porous material, including for example open-celled foams such as polyethylene or polyurethane. In some cases, one or more of the upper and lower channel layers can be comprised of a fabric, for example a knitted or woven spacer fabric (such as a knitted polyester 3D fabric, Baltex 7970®, or Gehring 879®) or a nonwoven material, or terry-woven or loop-pile materials. The fibers may not necessarily be woven, and can include felted and flocked (including materials such as Flotex®) fibrous materials. The materials selected are preferably suited to channeling wound exudate away from the wound and for transmitting negative pressure or vented air to the wound site, and can also confer a degree of kinking or occlusion resistance to the channel layers. In one example, the upper channel layer can include an open-celled foam such as polyurethane, and the lower channel layer can include a fabric. In another example, the upper channel layer is optional, and the system can instead be provided with an open upper channel. The upper channel layer can have a curved, rounded or upwardly convex upper surface and a substantially flat lower surface, and the lower channel layer can have a curved, rounded or downwardly convex lower surface and a substantially flat upper surface.

The fabric or material of any components of the bridge 130 can have a three-dimensional (3D) structure, where one or more types of fibers form a structure where the fibers extend in all three dimensions. Such a fabric can in some cases aid in wicking, transporting fluid or transmitting negative pressure. In some cases, the fabric or materials of the channels can include several layers of material stacked or layered over each other, which can in some cases be useful in preventing the channel from collapsing under the application of negative pressure. The materials used in some implementations of the conduit 108 can be conformable and pliable, which can, in some cases, help to avoid pressure ulcers and other complications which can result from a wound treatment system being pressed against the skin of a patient.

The distal ends of the upper, intermediate, and lower layers and the channel layers can be enlarged at their distal ends (to be placed over a wound site), and can form a "teardrop" or other enlarged shape. The distal ends of at least the upper, intermediate, and lower layers and the channel layers can also be provided with at least one through aperture. This aperture can be useful not only for the drainage of wound exudate and for applying negative pressure to the wound, but also during manufacturing of the device, as these apertures can be used to align these respective layers appropriately.

In some implementations, a controlled gas leak 146 (sometimes referred to as gas leak, air leak, or controlled air leak) can be disposed on the bridge portion 130, for example at the proximal end thereof. This air leak 146 can comprise an opening or channel extending through the upper layer of the bridge portion 130, such that the air leak 146 is in fluidic communication with the upper channel of the bridge portion 130. Upon the application of suction to the conduit 108, gas (such, as air) can enter through the gas leak 146 and move from the proximal end of the bridge portion 130 to the distal end of the bridge portion along the upper channel of the bridge portion 130. The gas can then be suctioned into the lower channel of the bridge portion 130 by passing through the apertures through the distal ends of the upper, intermediate, and lower layers.

The air leak 146 can include a filter. Preferably, the air leak 146 is located at the proximal end of the bridge portion 130 so as to minimize the likelihood of wound exudate or other fluids coming into contact and possibly occluding or interfering with the air leak 146 or the filter. In some instances, the filter can be a microporous membrane capable of excluding microorganisms and bacteria, and which may be able to filter out particles larger than 45 μm. Preferably, the filter can exclude particles larger than 1.0 μm, and more preferably, particles larger than 0.2 μm. Advantageously, some implementations can provide for a filter that is at least partially chemically-resistant, for example to water, common household liquids such as shampoos, and other surfactants. In some cases, reapplication of vacuum to the suction adapter or wiping of the exposed outer portion of the filter may be sufficient to clear any foreign substance occluding the filter. The filter can be composed of a suitably-resistant polymer such as acrylic, polyethersulfone, or polytetrafluoroethylene, and can be oleophobic or hydrophobic. In some cases, the gas leak 146 can supply a relatively constant gas flow that does not appreciably increase as additional negative pressure is applied to the conduit 108. In instances of the negative pressure wound treatment system 100 where the gas flow through the gas leak 146 increases as additional negative pressure is applied, preferably this increased gas flow will be minimized and not increase in proportion to the negative pressure applied thereto. Further description of such bridges, conduits, air leaks, and other components, features, and details that can be used with any implementations of the negative pressure wound treatment systems disclosed herein are found in U.S. Pat. No. 8,801,685, which is incorporated by reference in its entirety as if fully set forth herein.

Any of the wound therapy devices (such as, the device 110 or 110') disclosed herein can provide continuous or intermittent negative pressure therapy. Continuous therapy can be delivered at above 0 mmHg, −25 mmHg, −40 mmHg, −50 mmHg, −60 mmHg, −70 mmHg, −80 mmHg, −90 mmHg, −100 mmHg, −120 mmHg, −125 mmHg, −140 mmHg, −160 mmHg, −180 mmHg, −200 mmHg, or below −200 mmHg. Intermittent therapy can be delivered between low and high negative pressure set points (sometimes referred to as setpoint). Low set point can be set at above 0 mmHg, −25 mmHg, −40 mmHg, −50 mmHg, −60 mmHg, −70 mmHg, −80 mmHg, −90 mmHg, −100 mmHg, −120 mmHg, −125 mmHg, −140 mmHg, −160 mmHg, −180 mmHg, or below −180 mmHg. High set point can be set at above −25 mmHg, −40 mmHg, −50 mmHg, −60 mmHg, −70 mmHg, −80 mmHg, −90 mmHg, −100 mmHg, −120 mmHg, −125 mmHg, −140 mmHg, −160 mmHg, −180 mmHg, −200 mmHg, or below −200 mmHg. During intermittent therapy, negative pressure at low set point can be delivered for a first time duration, and upon expiration of the first time duration, negative pressure at high set point can be delivered for a second time duration. Upon expiration of the second time duration, negative pressure at low set point can be delivered. The first and second time durations can be same or different values.

In operation, the wound filler 102 can be inserted into the cavity of the wound 104, and wound cover 106 can be placed so as to seal the wound 104. The wound therapy device 110' can provide negative pressure to the wound cover 106, which can be transmitted to the wound 104 via the wound filler 102. Fluid (such as, wound exudate) can be drawn through the conduit 108' and stored in a canister. In some cases, fluid is absorbed by the wound filler 102 or one or more absorbent layers (not shown).

Wound dressings that can be utilized with the pump assembly and systems of the present application include Renasys-F, Renasys-G, Renasys AB, and Pico Dressings available from Smith & Nephew. Further description of such wound dressings and other components of a negative pressure wound therapy system that can be used with the pump assembly and systems of the present application are found in U.S. Patent Publication Nos. 2012/0116334, 2011/0213287, 2011/0282309, 2012/0136325, U.S. Pat. No. 9,084,845, and International App. No. PCT/EP2020/078376, each of which is incorporated by reference in its entirety as if fully set forth herein. In some cases, other suitable wound dressings can be utilized.

Figure 2A:
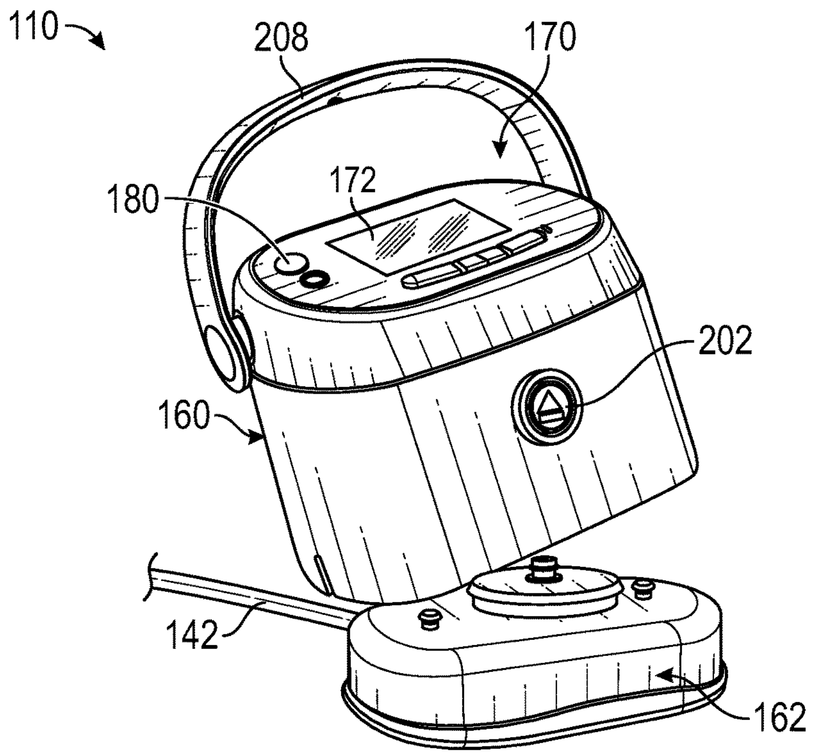
FIG. 2A is an isometric view of a negative pressure wound therapy device and canister, showing the canister detached from the pump assembly of the device.
Figure 2B:
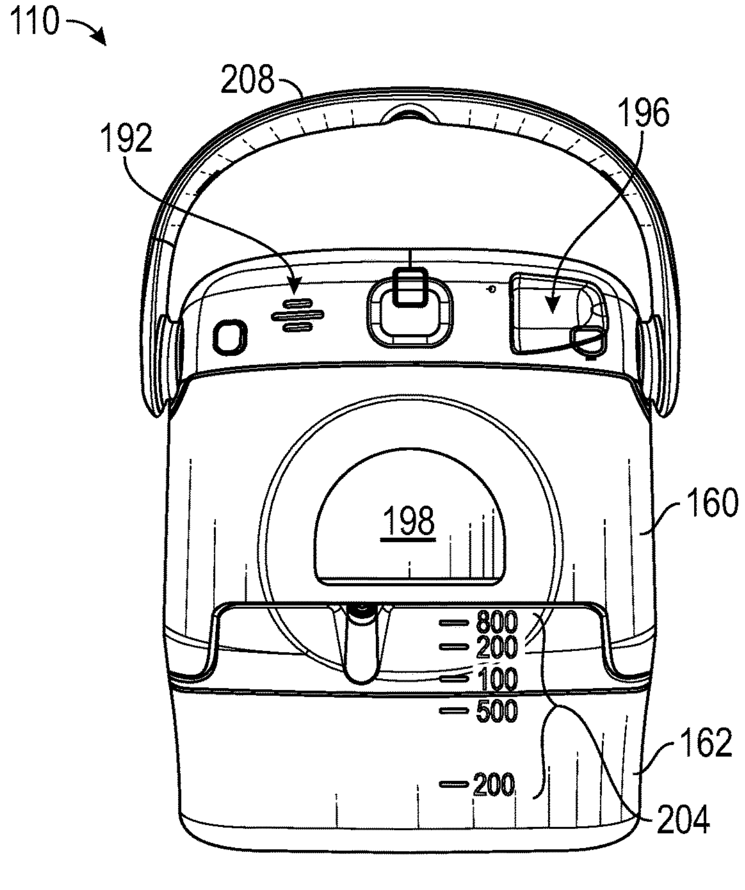
FIG. 2B is a back view of the negative pressure wound therapy device shown in FIG. 2A.
Figure 2C:
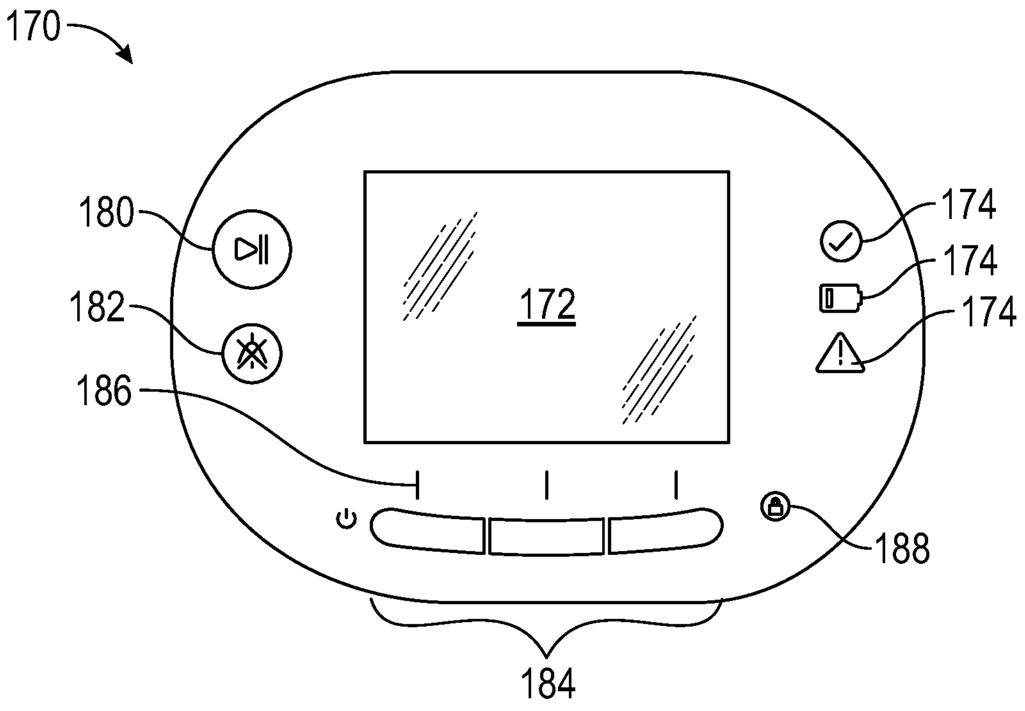
FIG. 2C illustrates a top surface of the negative pressure wound therapy device shown in FIG. 2A, showing a user interface.

FIGS. 2A-2C show the negative pressure wound therapy device 110. As illustrated, a pump assembly 160 and canister 162 can be connected, thereby forming the wound therapy device 110. With reference to FIG. 2C, the pump assembly 160 can include an interface panel 170 having a display 172, one or more indicators 174, or one or more controls or buttons, including, for example and without limitation, a therapy start and pause button 180 or an alarm/alert mute button 182. The interface panel 170 can have one or more input controls or buttons 184 (three being shown) that can be used to control any functions of the pump assembly 160 or the interface panel 170. For example and without limitation, one or more of the buttons 184 can be used to turn the pump assembly 160 on or off, to start or pause therapy, to operate and monitor the operation of the pump assembly 160, to scroll through menus displayed on the display 172, or to control or perform other functions. In some cases, the command buttons 184 can be programmable, and can be made from a tactile, soft rubber.

Additionally, the interface panel 170 can have visual indicators 186 that can indicate which of the one or more buttons 184 is active. The interface panel 170 can also have a lock/unlock control or button 188 that can be configured to selectively lock or unlock the functionality of the various buttons (e.g., buttons 184) or the display 172. For example, therapy setting adjustment can be locked/unlocked via the lock/unlock control 188. When the lock/unlock button 188 is in the locked state, depressing one or more of the various other buttons or the display will not cause the pump assembly 160 to change any display functions or performance functions of the device. This way, the interface panel 170 will be protected from inadvertent bumping or touching of the various buttons or display. The interface panel 170 can be located on an upper portion of the pump assembly 160, for example and without limitation on an upward facing surface of the pump assembly 160.

The display 172, which can be a screen such as an LCD screen, can be mounted in a middle portion of the interface panel 170. The display 172 can be a touch screen display. The display 172 can support playback of audiovisual (AV) content, such as instructional videos, and render a number of screens or graphical user interfaces (GUIs) for configuring, controlling, and monitoring the operation of the pump assembly 160.

The one or more indicators 174 can be lights (such as, LEDs) and can be configured to provide a visual indication of alarm conditions and or a status of the pump. For example and without limitation, the one or more indicators 174 can be configured to provide a visual indication of a status of the pump assembly 160 or other components of the negative pressure wound treatment system 100, including without limitation the conduit 108 or the wound cover 106 (such as, to provide an indication of normal operation, low battery, a leak, canister full, blockage, overpressure, or the like). Any one or more suitable indicators can be additionally or alternatively used, such as visual, audio, tactile indicator, and so on.

FIG. 2B shows a back or rear view of the wound therapy device 110 shown in the FIG. 2A. As shown, the pump assembly 160 can include a speaker 192 for producing sound. For example and without limitation, the speaker 192 can generate an acoustic alarm in response to deviations in therapy delivery, non-compliance with therapy delivery, or any other similar or suitable conditions or combinations thereof. The speaker 192 can provide audio to accompany one or more instructional videos that can be displayed on the display 172.

The pump assembly 160 can be configured to provide easy access (such as, an access door on the casing of the pump assembly) to one or more filters of the pump assembly 160, such as antibacterial filters. This can enable a user (such as, a healthcare provider or patient) to more easily access, inspect or replace such filters. The pump assembly 160 can also include a power jack 196 for providing power to the pump assembly 160 or for charging and recharging an internal power source (such as, a battery). Some implementations of the pump assembly 160 can include a disposable or renewable power source, such as one or more batteries, so that no power jack is needed. The pump assembly 160 can have a recess 198 formed therein to facilitate gripping of the pump assembly 160.

The canister 162 can hold fluid aspirated from the wound 104. For example, the canister 162 can have an 800 mL (or approximately 800 mL) capacity, or from a 300 mL or less capacity to a 1000 mL or more capacity, or any capacity level in this range. The canister 162 can include a tubing for connecting to the conduit 108 in order to form a fluid flow path. The canister 162 can be replaced with another canister, such as when the canister 162 has been filled with fluid. With reference to FIG. 2A, the wound therapy device 110 can include a canister inlet tube 142 (also referred to herein as a dressing port connector) in fluid communication with the canister 162. For example and without limitation, the canister inlet tube 142 can be used to connect with the conduit 108.

The canister 162 can be selectively coupleable and removable from the pump assembly 160. With reference to FIG. 2A, in some cases, a canister release button 202 can be configured to selectively release the canister 162 from the pump assembly 160. With reference to FIG. 2B, the canister 162 can have one or more fill lines or graduations 204 to indicate to the user and amount of fluid or exudate stored within the canister 162.

The wound therapy device 110 can have a handle 208 that can be used to lift or carry the wound therapy device 110. The handle 208 can be coupled with the pump assembly 160 and can be rotatable relative to the wound therapy device 110 so that the handle can be rotated upward for lifting or carrying the wound therapy device 110 or the pump assembly 160, or rotated into a lower profile in a more compact position when the handle is not being used. In some cases, the handle 208 can be coupled with the pump assembly 160 in a fixed position. The handle 208 can be coupled with an upper portion of the pump assembly 160 or can be removable from the wound therapy device 110.

Figure 3:
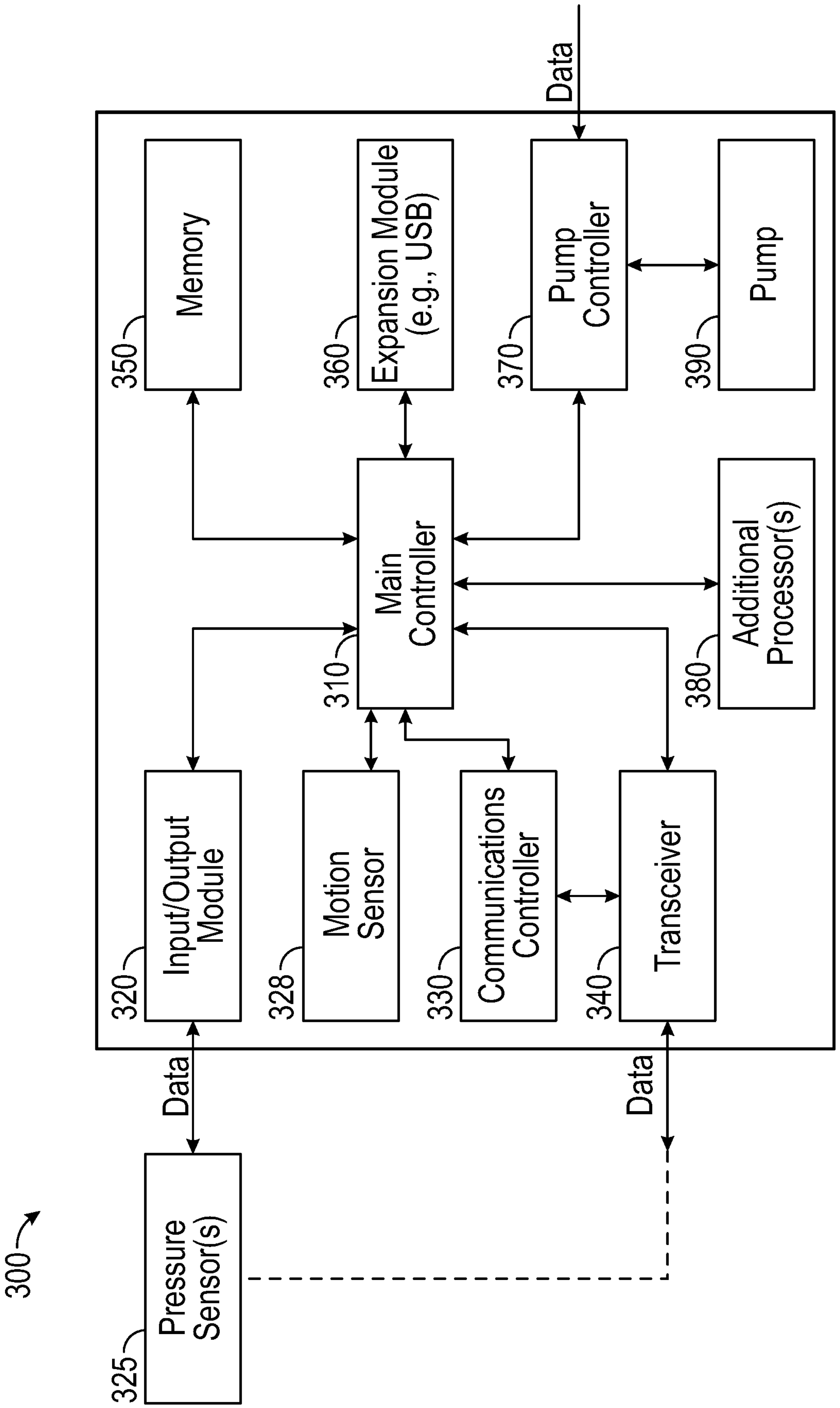
FIG. 3 illustrates a schematic of a control system of a negative pressure wound therapy device.

FIG. 3 illustrates a schematic of a control system 300 that can be employed in any of the wound therapy devices described herein, such as in the wound therapy device 110. Electrical components can operate to accept user input, provide output to the user, operate the pressure source, provide connectivity, and so on. A first processor (such as, a main controller 310) can be responsible for user activity, and a second processor (such as, a pump controller 370) can be responsible for controlling another device, such as a pump 390.

An input/output (I/O) module 320 can be used to control an input and/or output to another component or device, such as the pump 390, one or more sensors (for example, one or more pressure sensors 325 configured to monitor pressure in one or more locations of the fluid flow path), or the like. For example, the I/O module can receive data from one or more sensors through one or more ports, such as serial (for example, I2C), parallel, hybrid ports, and the like. Any of the pressure sensors can be part of the wound therapy device or the canister. In some cases, any of the pressure sensors 325 can be remote to the wound therapy device, such as positioned at or near the wound (for example, in the dressing or the conduit connecting the dressing to the wound therapy device). In such implementations, any of the remote pressure sensors can communicate with the I/O module over a wired connection or with one or more transceivers 340 over a wireless connection.

One or more motion sensors 328 can monitor motion of the wound therapy device. The one or more motion sensors 328 can include one or more acceleration sensors or accelerometers (such as, one or more MEMS accelerometers, which can be part of a MEMS accelerometer integrated circuit), gyroscopes, or the like. Any of the accelerometers can be a three-axis accelerometer, a piezoelectric accelerometer, or the like. The one or more motion sensors 328 can provide motion data to the main controller 310. The one or more motions sensors 328 can be powered by the internal power source. For instance, the one or more motions sensors 328 can be directly receive power from the internal power source so that the one or more motion sensors 328 remain operational when the device is off (such as, when the device is in storage, transit, or otherwise not in use). In some cases, the one or more motion sensors 328 can be powered by another power source so that the one or more motion sensors 328 remain operational when the internal power source has been depleted. One or more motions sensors 328 can be low-power devices (such as, low-power MEMS accelerometer integrated circuits).

The main controller 310 can receive data from and provide data to one or more expansion modules 360, such as one or more USB ports, SD ports, Compact Disc (CD) drives, DVD drives, FireWire ports, Thunderbolt ports, PCI Express ports, and the like. The main controller 310, along with other controllers or processors, can store data in memory 350 (such as one or more memory modules), which can be internal or external to the main controller 310. Any suitable type of memory can be used, including volatile or non-volatile memory, such as RAM, ROM, magnetic memory, solid-state memory, Magnetoresistive random-access memory (MRAM), and the like.

The main controller 310 can be a general purpose controller, such as a low-power processor or an application specific processor. The main controller 310 can be configured as a "central" processor in the electronic architecture of the control system 300, and the main controller 310 can coordinate the activity of other processors, such as the pump controller 370, one or more communications controllers 330, and one or more additional processors 380. The main controller 310 can run a suitable operating system, such as a Linux, Windows CE, VxWorks, etc.

The pump controller 370 can control the operation of a pump 390, which can generate negative or reduced pressure. The pump 390 can be a suitable pump, such as a diaphragm pump, peristaltic pump, rotary pump, rotary vane pump, scroll pump, screw pump, liquid ring pump, diaphragm pump operated by a piezoelectric transducer, voice coil pump, and the like. The pump controller 370 can measure pressure in a fluid flow path, using data received from one or more pressure sensors 325, calculate the rate of fluid flow, and control the pump. The pump controller 370 can control the pump actuator (such as, a motor) so that a desired level of negative pressure is achieved in the wound 104. The desired level of negative pressure can be pressure set or selected by the user. The pump controller 370 can control the pump (for example, pump motor) using pulse-width modulation (PWM) or pulsed control. A control signal for driving the pump can be a 0-100% duty cycle PWM signal. The pump controller 370 can perform flow rate calculations and detect alarms. The pump controller 370 can communicate information to the main controller 310. The pump controller 370 can be a low-power processor.

Any of the one or more communications controllers 330 can provide connectivity (such as, a wired or wireless connection 332). The one or more communications controllers 330 can utilize one or more transceivers 340 for sending and receiving data. The one or more transceivers 340 can include one or more antennas, optical sensors, optical transmitters, vibration motors or transducers, vibration sensors, acoustic sensors, ultrasound sensors, or the like. Any of the one or more transceivers 340 can function as a communications controller. In such case, the one or more communications controllers 330 can be omitted. Any of the one or more transceivers 340 can be connected to one or more antennas that facilitate wireless communication. The one or more communications controllers 330 can provide one or more of the following types of connections: Global Positioning System (GPS), cellular connectivity (for example, 2G, 3G, LTE, 4G, 5G, or the like), NFC, Bluetooth connectivity (or BLE), radio frequency identification (RFID), wireless local area network (WLAN), wireless personal area network (WPAN), WiFi connectivity, Internet connectivity, optical connectivity (for example, using infrared light, barcodes, such as QR codes, etc.), acoustic connectivity, ultrasound connectivity, or the like. Connectivity can be used for various activities, such as pump assembly location tracking, asset tracking, compliance monitoring, remote selection, uploading of logs, alarms, and other operational data, and adjustment of therapy settings, upgrading of software or firmware, pairing, and the like.

Any of the one or more communications controllers 330 can provide dual GPS/cellular functionality. Cellular functionality can, for example, be 3G, 4G, or 5G functionality. The one or more communications controllers 330 can communicate information to the main controller 310. Any of the one or more communications controllers 330 can include internal memory or can utilize memory 350. Any of the one or more communications controllers 330 can be a low-power processor.

The control system 300 can store data, such as GPS data, therapy data, device data, and event data. This data can be stored, for example, in memory 350. This data can include patient data collected by one or more sensors. The control system 300 can track and log therapy and other operational data. Such data can be stored, for example, in the memory 350.

Using the connectivity provided by the one or more communications controllers 330, the control system 300 can upload any of the data stored, maintained, or tracked by the control system 300 to a remote computing device, such as the device 334. The control system 300 can also download various operational data, such as therapy selection and parameters, firmware and software patches and upgrades, and the like (for example, via the connection to the device 334). The one or more additional processors 380, such as processor for controlling one or more user interfaces (such as, one or more displays), can be utilized. In some cases, any of the illustrated or described components of the control system 300 can be omitted depending on an embodiment of a wound monitoring or treatment system in which the control system 300 is used.

Any of the negative pressure wound therapy devices described herein can include one or more features disclosed in U.S. Pat. No. 9,737,649 or U.S. Patent Publication No. 2017/0216501, each of which is incorporated by reference in its entirety.

Multiple Dressing Negative Wound Therapy

Figure 4:
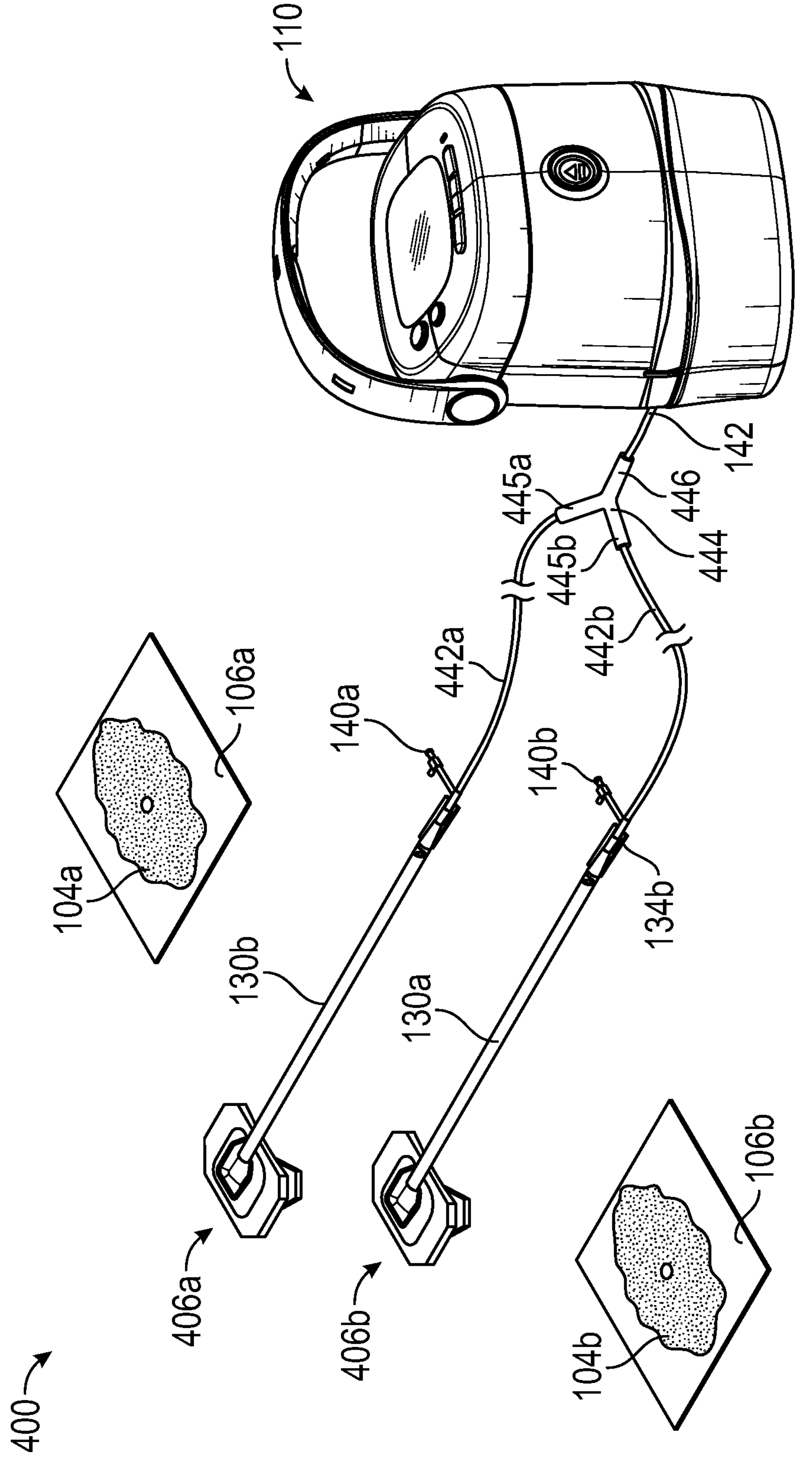
FIG. 4 illustrates another negative pressure wound therapy system.

FIG. 4 illustrates another negative pressure wound treatment system 400. The system 400 can include a wound therapy device capable of supplying negative pressure to the wound site or sites, such as wound therapy device 110. The wound therapy device 110 can be in fluidic communication with one or more wound dressings 406*a*, 406*b* (collectively referred to as 406) so as to supply negative pressure to one or more wounds, such as the wounds 104*a* and 104*b*. A first fluid flow path can include components providing fluidic connection from the wound therapy device 110 to the first wound dressing 406*a*. As a non-limiting example, the first fluid flow path can include the path from the wound dressing 406*a* to the wound therapy device 110 or the path from the first wound dressing 406*a* to an inlet 446 of a branching attachment (or connector) 444 in fluidic connection with the wound therapy device 110. Similarly, a second fluid flow path can include components providing fluidic connection from the wound therapy device 110 to the second wound dressing 406*b*.

The system 400 can be similar to the system 100 with the exception that multiple wounds 104*a* and 140*b* are being treated by the system 400. The system 400 can include any one or more of the components of the system 100, which are illustrated in FIG. 4 with appended letter "a" or "b" to distinguish between the first and second wounds (such as, the wounds 104*a* and 104*b*, the covers 106*a* and 106*b*). As illustrated, the system 400 can include a plurality of wound dressings 406*a*, 406*b* (and corresponding fluid flow paths) in fluidic communication with the wound therapy device 110 via a plurality of suction adapters, such as the adapter 108. The suction adapters can include any one or more of the components of the adapter 108, which are illustrated in FIG. 4 with appended letter "a" or "b" to distinguish between the first and second wounds (such as, the bridge portions 130*a* and 130*b*, the connectors 134*a* and 134*b*, and the caps 140*a* and 140*b*).

The wound therapy device 110 can be fluidically coupled via the tube 142 with the inlet 446 of the connector 444. The connector 444 can be fluidically coupled via branches 445*a*, 445*b* and tubes or conduits 442*a*, 442*b* with the connectors 134*a*, 134*b*, which can be fluidically coupled with the tubes or conduits 130*a*, 130*b*. The tubes or conduits 130*a*, 130*b* can be fluidically coupled with the dressings 406*a*, 406*b*. Once all conduits and dressing components are coupled and operably positioned, the wound therapy device 110 can be activated, thereby supplying negative pressure via the fluid flow paths to the wounds 104*a*, 104*b*. Application of negative pressure can be applied until a desired level of healing of the wounds 104*a*, 104*b* is achieved. Although two wounds and wound dressing are illustrated in FIG. 4, some implementations of the wound therapy device 110 can provide treatment to a single wound (for instance, by closing the unused branch 445*a* or 445*b* of the connector 444) or to more than two wounds (for instance, by adding branches to the connector 444).

The system 400 can include one or more features disclosed in U.S. Patent Publication No. 2020/0069850 or International Publication No. WO2018/167199, each of which is incorporated by reference in its entirety.

Fall Detection and Device Orientation Detection

It can be advantageous to monitor movement of a negative pressure wound therapy device to determine whether the device has been dropped (or otherwise misused, such as incorrectly positioned), monitor movement of the device, or monitor movement of the patient. To accomplish this, one or more motions sensors (such as, one or more motion sensors 328) can be utilized. Data from the one or more motion sensors can be provided one or more controllers (such as, the main controller 310), which can detect that the device has been dropped (or otherwise misused). In some cases, one or more motion sensors can be part of a device or package (such as, an integrated circuit) that provides processing capabilities for analyzing the data detected by the one or more motion sensors. An indication of a drop (or misuse) can be provided, as described herein.

Figure 5:
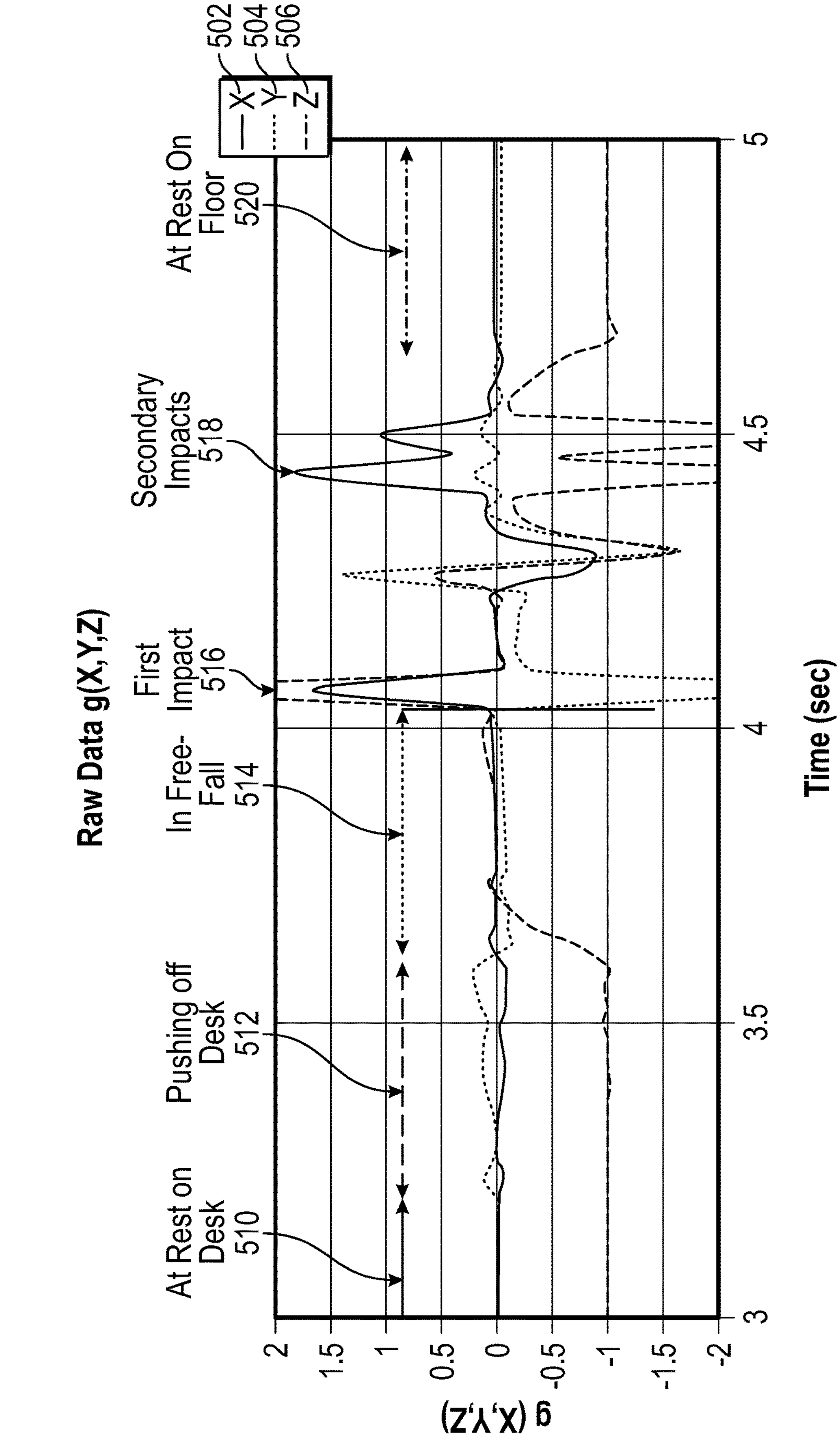
FIGS. 5 to 8 illustrate plots of acceleration versus time.

A drop (or free fall) can be associated with a reduced gravitational force measured by one or more motion sensors, such as one or more accelerometers or gyroscopes. FIG. 5 illustrates a plot of acceleration measured by a three-axis accelerometer of a negative pressure wound therapy device versus time. Such accelerometer can measure acceleration along the x-axis (illustrated as 502 in FIG. 5), y-axis (illustrated as 504 in FIG. 5), and z-axis (illustrated as 506 in FIG. 5). During time period 510, the device is resting on a surface (such as, a desk). During this time period, acceleration along the x-axis and y-axis is 0 g (where $g=9.8\ m/s^2$), while a constant gravitational acceleration of −1 g is observed along the z-axis (acceleration is negative due to the orientation of the device; in some cases, the acceleration along the z-axis may be 1 g). During time period 512, the device is being pushed off the surface. During this time period, the acceleration along x-axis, y-axis, and z-axis remains unchanged.

During time period 514, the device is in free fall. Acceleration along the x-axis and y-axis remains unchanged, while acceleration along the z-axis decreases to 0 g (due the device being in free fall). In some cases, free fall causes a "near zero-G" condition (or event), which can be an indication of a drop or misuse. Such near zero-G condition can be preceded by a "low-G" condition (or event) when acceleration along the z-axis decreases. During the free fall, acceleration values along the three axis remain at zero until impact with the floor (or another surface) occurs (at around 4 seconds as shown in FIG. 5).

During time period 516, the device makes a first impact with the floor (or another surface). During this time period, acceleration values along the three axis are large (positive or negative) values as the gravitational force increases when the device lands on the surface. Such "high-G" event (or condition) is indicative of the device decelerating on contact with a hard surface. During time period 518, the device makes one or more secondary impacts with the floor (or another surface). These one or more secondary impacts can be due to the device bouncing or rolling. As is illustrated by multiple peaks during the time period 518, the device has made several secondary impacts with the surface. During this time period, acceleration values along the three axis are large (positive or negative) values. Finally, during time period 520 the device is at rest on the floor (or another surface). Similarly to the time period 510, during this time period acceleration along the x-axis and y-axis is 0 g, while a constant gravitational acceleration of −1 g is observed along the z-axis.

Figure 6:
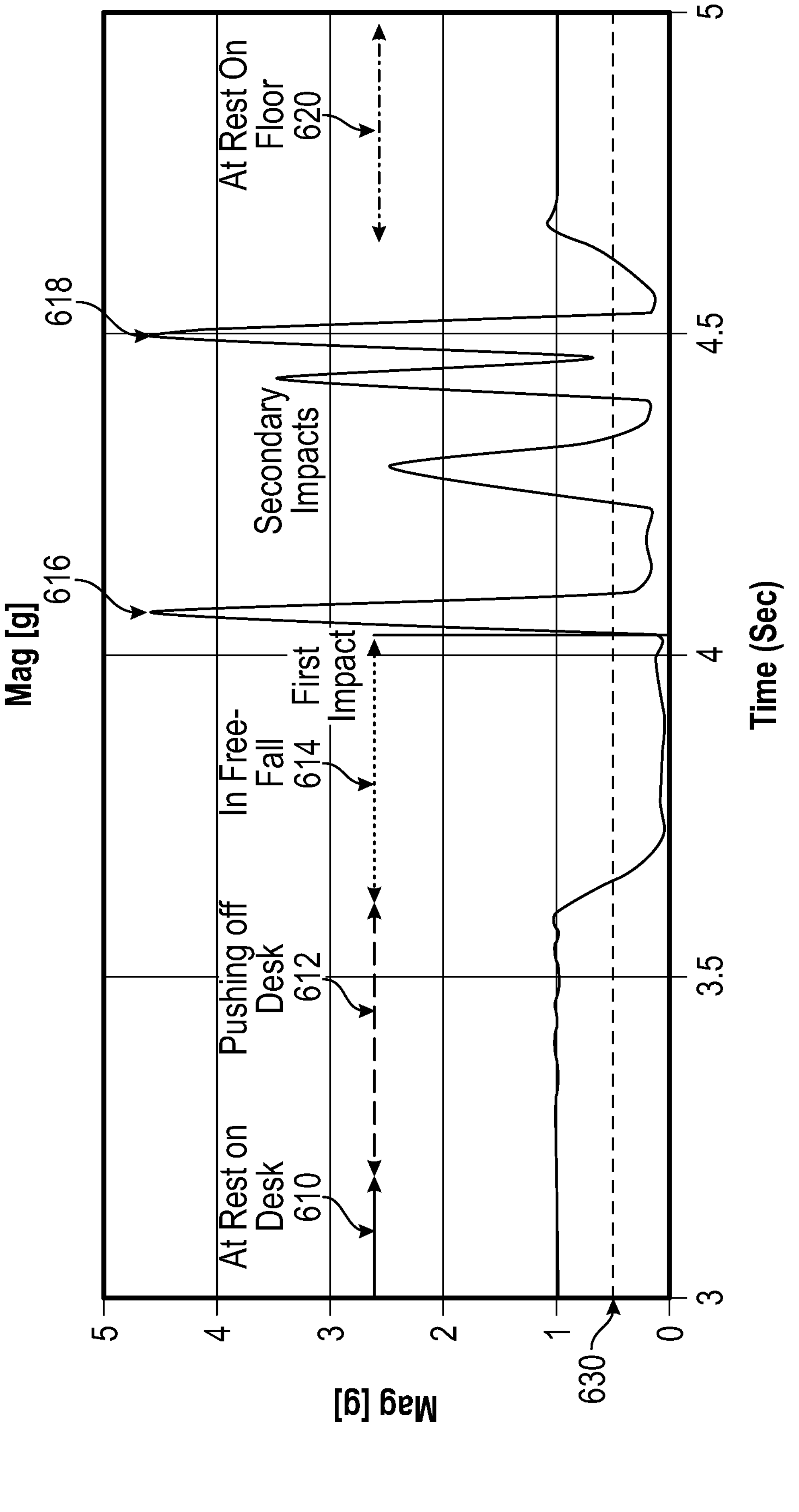

FIG. 6 illustrates plot of the magnitude of acceleration measured by the three-axis accelerometer versus time. Magnitude of acceleration (|g|) can be determined according to the following equation ($g_x$, $g_y$, and $g_z$ are the acceleration values along x-axis, y-axis, and z-axis respectively):

$$|g| = \sqrt{g_x^2 + g_y^2 + g_z^2}$$

Time durations 610, 612, 614, 616, 618, and 620 in FIG. 6 correspond to time durations 510, 512, 514, 516, 518, and 520 in FIG. 5. As is illustrated by the time duration 614, when the device is in free fall the magnitude of acceleration decreases to and remains at 0 g.

One or more of a filter or threshold analysis can be applied to the acceleration data (such as, to the magnitude of acceleration data) to determine whether the device is in free fall or detect smaller movements (such as, lifting the device or placing the device down on a surface). Careful consideration for the threshold (sometimes referred to as a low acceleration threshold) may be needed to avoid any false positives (since, for example, a potential trigger may be lifting or placing down the device too quickly). In some cases, the threshold to detect free fall from the magnitude of acceleration can be between about 0.5 and 0.4 (or another suitable value indicative of a low-G condition). For instance, the device can be determined to be in free fall while the magnitude of acceleration satisfies the threshold (such as, while the magnitude of acceleration meets and/or remains below the threshold). FIG. 6 illustrates a threshold 630 of about 0.5. During the time duration 614 (when the device is in free fall), the magnitude of acceleration equals to or remains below the threshold 630.

In some implementations, the height of the drop (or fall) can be determined. This can be accomplished by determining the time duration of the device being in free fall (such as, the time duration 614). The height of the drop (h) can be calculated using the following equation (g is the free fall acceleration (9.8 $m/s^2$) and t is the duration of free fall):

$$h = (1/2)gt^2$$

An indication of one or more of the duration of the fall or height of fall can be provided.

Measuring the duration (and/or height) of free fall can provide advantages over approaches that rely of detecting the instantaneous shock at impact for fall detection. For example, the duration of the free fall can serve as a check on the detection of whether the device is in free fall. A threshold duration can be used to differentiate false positives from the actual free fall. In some cases, if the determined duration of possible free fall does not satisfy the threshold duration (for instance, is shorter than the threshold duration), a determination of a false positive can be made. Advantageously, accuracy of the fall detection can be improved.

In some cases, the location of the accelerometer can be offset from the center of mass of the device. For example, with reference to FIG. 3, the accelerometer (illustrated as 328) can be positioned on a substrate (such as, a printed circuit board (PCB)) of the control system 300. With reference to FIG. 2B, the PCB can be positioned within a housing of the pump assembly 160 at a location that is offset from the center of mass of the device. The center of mass of the device can change depending on the fill level of the canister.

Figure 7:
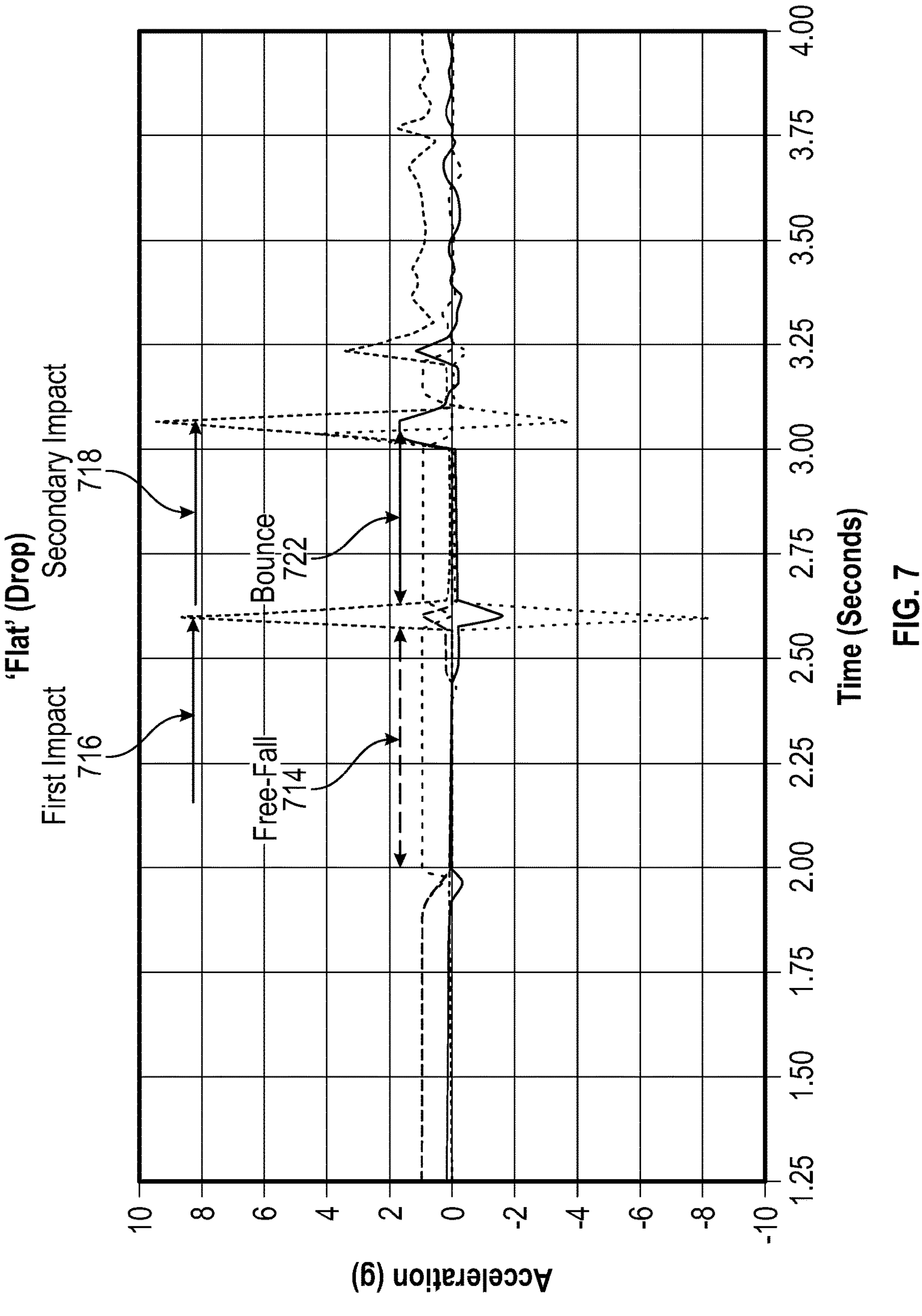

Because the center of mass of the device can be offset from the location of the accelerometer, a drop or fall can be either flat (when the device does not rotate) or rotating (when the device rotates about the center of mass). In practice, many falls can be rotating falls. As described herein, a flat fall can be detected by determining that the magnitude of acceleration satisfies a threshold indicative of a low-G condition. This is illustrated in FIG. 7, which is similar to FIG. 5. Free fall is indicted by time duration 714 during which the magnitude of acceleration remains at or below a threshold. First and secondary impacts are indicated by 716 and 718. Time duration during which the device bounces on the surface (such as, the floor) after the first impact is illustrated as 722.

A rotating fall can cause the accelerometer to detect centripetal acceleration (a) caused by the device velocity of rotation (v) and the offset of the accelerometer from the axis of rotation (r) according to:

$$a = v^2 / r$$

Figure 8:
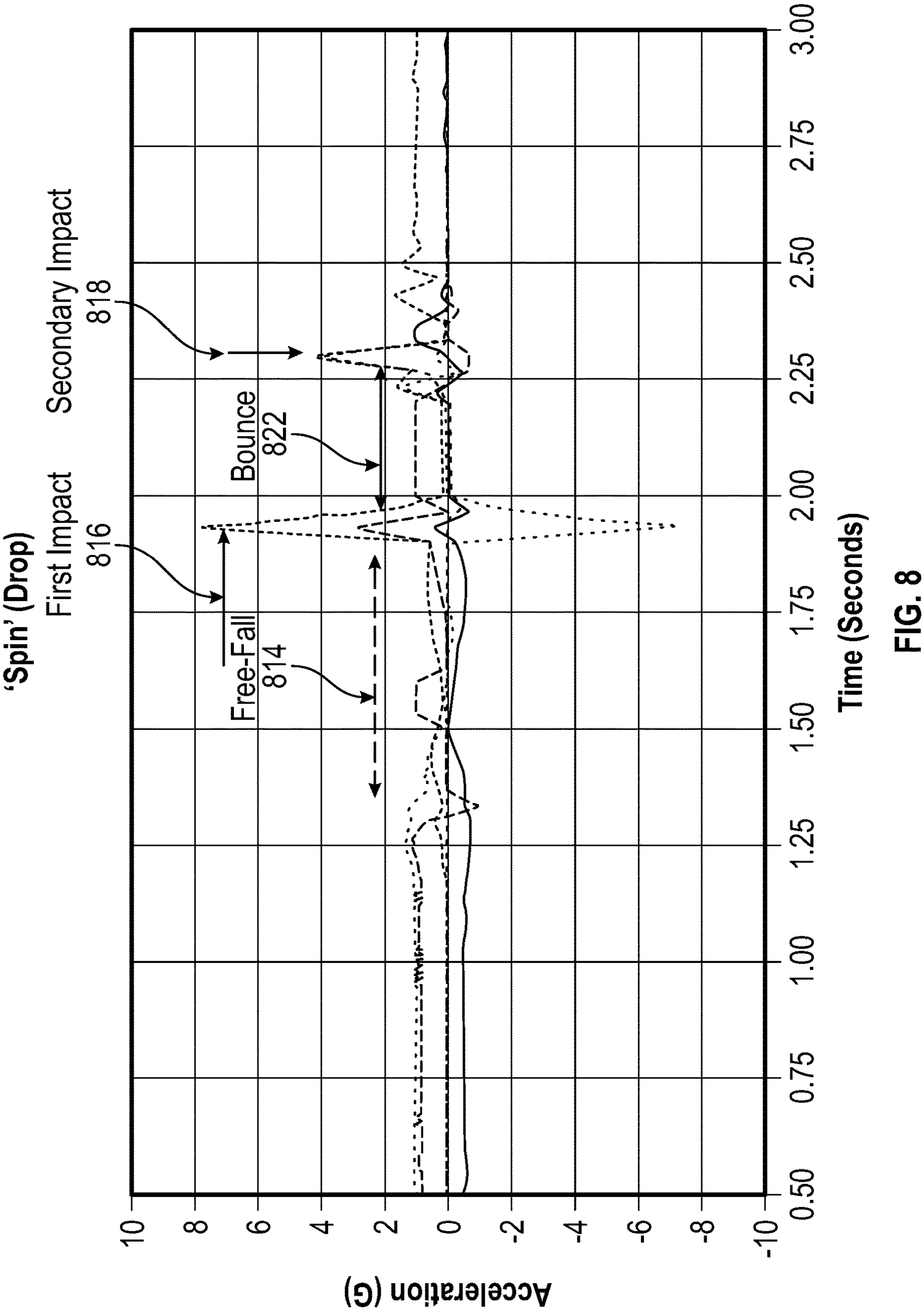

This acceleration value can be significant enough to disrupt the threshold analysis as shown in FIG. 8 (which is similar to FIG. 7, but illustrates a plot that captures a rotating fall). As is shown by time duration 814, during which the device is in free fall, the magnitude of acceleration can exceed the low acceleration threshold due to the extra contribution(s) of centripetal acceleration. Acceleration values during time duration 814 are not as flat and constant as during the time duration 714. For instance, a bump in the acceleration values is shown during the time duration 714. Such centripetal acceleration contribution(s) can cause the drop to be missed or the duration (and the drop height) to be determined incorrectly (such as, underestimated).

To account for the device possibly rotating (or spinning) during the drop, free fall detection can be refined as follows:

1. Detect the time of first impact as evidenced by the high-G event.
2. Disallow any further incoming data from triggering for 1 second (or another suitable time period), as these events are likely to be caused by secondary impacts.
3. Search data captured by the accelerometer for the initiation time of the low-G event.
4. Calculate the drop height based on time separation between 1 and 3.

In some cases, any of the steps (such as, step 2) can be omitted and/or the steps can be performed in a different order.

First impact can be detected by detecting that the acceleration (such as, the magnitude of acceleration) satisfies a high acceleration threshold. For instance, with reference to FIG. 6, during the first impact shown as 616, the magnitude of acceleration reaches a large value (such as, around 4.5). The high acceleration threshold can be set to 4.0 or another suitable value. As another example, during the impact, the rate of change of the magnitude of acceleration is large (as shown by the slope of the peak 616). A rate of change threshold can be used to detect the impact. Once the time duration between detection of free fall (step 3 above) and first impact (step 1 above) has been determined, the height of the drop can be calculated, as described above.

Selecting the appropriate frequency at which the accelerometer is sampled (or at which accelerometer data is obtained) can be important for ensuring calculation accuracy and resolution of the fall height. However, there is a trade-off since higher sampling frequencies increase the power consumption of the accelerometer. For example, MEMS accelerometers can be sampled at varying frequencies from 10's of Hertz to several kilohertz. In some configurations, testing has revealed that the sampling rate of about 50 Hertz can yield sufficient resolution and accuracy while not consuming excessive power. In some implementations, other suitable sampling rates can be used.

As described herein, an indication of a drop can be provided responsive to detecting a fall. In some cases, the indication can include, responsive to the detection of a fall, pausing the delivery of negative pressure wound therapy (for instance, by turning off the negative pressure source) or reducing the intensity of the therapy (for instance, by lowering power provided to the negative pressure source). Advantageously, this can reduce patient discomfort (which can be caused, for instance, by the negative pressure source attempting to maintain desired pressure at the wound when the wound dressing or another portion of the fluid flow path has been dislodged or disconnected as a result of the fall), reduce noise (for example, from operation of the negative pressure source or activation of one or more audible alarms, such as a leak alarm), or the like.

In certain cases, responsive to detecting a fall, the device can initiate one or more self-tests to ensure that the device can properly provide negative pressure wound therapy. Additional details of self-testing are disclosed in International Publication No. WO2021/191203, titled "Self-Testing for Negative Pressure Wound Therapy Devices," which is incorporated by reference in its entirety. In some cases, the device can prevent provision of negative pressure wound therapy responsive to detecting a fall (for instance, responsive to detecting a fall from a large height, which can result in a high likelihood of damage to the device) and/or responsive to determining that one or more self-tests has failed. Additional or alternative safety mechanisms can be activated responsive to detection of a fall.

In some instances, fall detection can be performed when the device is off (such as, in storage, transit, transport, or otherwise not in use). As described herein, the accelerometer can receive power directly from the internal power source (or another power source). This way, the accelerometer can monitor device movement even when other electronic components (such as, the main controller 310) are not operating (for example, powered down or in a sleep state). As described herein, the accelerometer can be part of a package that provides processing capabilities. Detection of one or more of a low-G or a high-G event can cause the accelerometer package to wake-up the main controller 310 or another one or more electronic components of the device (for instance, via asserting or triggering one or more interrupts). One or more remedial actions (such as, providing an indication, pausing therapy, or the like) can be taken, as described herein.

Device orientation can be detected using any of the approached described herein. For example, inverted device orientation can be detected via the analysis of the acceleration values along one or more of x-axis, y-axis, or z-axis. The acceleration value along the z-axis would be 1 g when the device is upside down and resting on a surface (rather than −1 g as illustrated during time duration 510 in FIG. 5). Undesirable tilt may be detected if one (or more than one) accelerometer axes satisfies (such as, equals and/or exceeds) a threshold value. For instance, when the device is standing upright on a surface, acceleration value along the z-axis would be around 1 (or, in some cases, −1 depending on the calibration of the accelerometer). When the device is tilted at 45 degrees, the acceleration value along the z-axis would be around 0.5 (or, in some cases, −0.5). If the device is laying on its side, the acceleration value along the z-axis would be around zero. When acceleration along the z-axis is negative (or, in some cases, positive), the device may be tilted beyond lying on its side. If acceleration along the z-axis is −1 (or, in some cases, +1), then the device is completely inverted. As a result, tilt detection can be performed based on determining that the acceleration along the z-axis satisfies (such as, equals or exceeds/falls below) a tilt threshold. In some cases, the tilt threshold can be 0.5 (or, in some cases, −0.5). The determination can be made using absolute values of the acceleration along the z-axis and the tilt threshold to obviate any dependency on the calibration of the accelerometer.

Detection of an undesirable tilt can cause the device to generate an indication to the user to place the device in the proper orientation (such as, an audible alert, a visual message, or the like). In some cases, the delivery of negative pressure wound therapy can be paused until the device has been placed in the proper orientation. This can prevent blockage of one or more filters (such as, a blockage of a filter in the canister, which would undesirably necessitate changing the canister). Additional or alternative safety mechanisms can be activated responsive to detection of incorrect device orientation.

Patient activity can be monitored using any of the approaches disclosed herein. For instance, patient mobility may be detected by examining the magnitude of acceleration to determine if a significant level of movement (as compared to a threshold) is detected over a significant time interval (as compared to a threshold). The level of activity may be summed to give a cumulative activity level metric. Tracking patient mobility (or lack of mobility) may be beneficial to health care providers for determining or adjusting treatment of the patient. Data related to patient activity can be communicated to a remote computing device, as described herein.

Accelerometer data can be analyzed to understand the frequency at which the device is in motion or travelling versus being stationary (such as, bedside). This analysis can lead to a more user-optimized design for negative pressure wound therapy devices. For example, if the accelerometer data suggests that users of devices are very mobile, a focus on the portability in the design would be desirable. As another example, if drop detection is triggered often, a design with a focus on durability may be preferable. Accelerometer data can allow for investigations to be performed to understand causes of user error or misuse, such as incorrect device orientation. Also, tracking the patient's mobility can provide helpful information for the health care provider (HCP) in determining the best course of treatment for the patient.

Advantageously, the approached described in this section can provide improved fall detection or misuse detection. As a result, patient comfort and safety can be promoted. In addition, mobility of the patient can be monitored, which can be used to refine treatment and develop more reliable and patient-friendly negative pressure wound therapy devices and to determine the best course of treatment for the patient.

Transitioning to a Different Therapy System

It can be advantageous to be able to determine and suggest that the patient may transition from a larger and heavier canister-enabled negative pressure wound therapy system (typically configured to treat larger wounds) to a smaller and more portable canisterless negative pressure wound therapy system (typically configured to treat smaller wounds). As the patient's wound is healing due to the application of negative pressure wound therapy, the size of the wound can be reduced and the amount of fluid that the wound exudes can become smaller. As a result, the patient may be able to transition to a canisterless system at some point during the treatment. One example of a canisterless system is the Pico system available from Smith & Nephew.

In some cases, the amount of fluid (such as, exudate) produced by the wound can be monitored. If the rate of fluid produced by the wound is low enough, transition to canisterless system (or mode) can be suggested. Approaches for accomplishing these goals are described below.

Any of the negative pressure wound therapy devices, such as the device 110, can communicate with any of the canisters disclosed herein, such as the canister 162. The device can retrieve data from the canister. Such data can include one or more of status data (such as, whether the canister is full or the level of fluid in the canister), configuration data (such as, canister capacity or size, for instance, 300 mL or 800 mL), identification data (such as, canister identifier, batch code, or serial number of the canister), date of manufacture of the canister (which can be a timestamp), date/time of first use of the canister (which can be a timestamp), or the like.

The retrieval of data can be performed by or under control of one or more controllers of the device. The retrieval of data can be performed via a wired connection or wirelessly, such as using one or more transceivers 340. For instance, the device can retrieve the data using a near-field protocol (such as, NFC), RFID, Bluetooth, or the like. The data can be retrieved prior to initiating negative pressure wound therapy.

Any of the canisters disclosed herein, such as the canister 162, can include electronics with memory (which can store any of the data described in this section) and communication capabilities. The electronics can be partially or fully positioned within the canister housing. The electronics can be powered by a power source, such as a coin cell battery or one or more capacitors. In some cases, external power can be provided, such as via NFC, RFID, or other wireless charging protocols.

Additional details of communicating with the canister and retrieving data are disclosed in International Patent Application No. PCT/EP2022/060464, filed on Apr. 20, 2022, and titled "Communication Systems and Methods for Negative Pressure Wound Therapy Devices," International Patent Application No. PCT/EP2022/060463, filed on Apr. 20, 2022, and titled "Canister Status Determination for Negative Pressure Wound Therapy Devices," and International Patent Application No. PCT/EP2022/060459, filed on Apr. 20, 2022, and titled "Intelligent Disposable Devices for Wound Therapy and Treatment," each of which is incorporated by reference in its entirety.

In some cases, the device can detect presence of a canister. For instance, the device can attempt to communicate with the canister and determine whether response has been received. As another example, the device can utilize a sensor, such as optical sensor, resistive sensor, capacitive sensor, magnetic sensor, or the like, to determine presence of the canister. As described herein, the device can retrieve data from the canister, including one or more of: canister serial number, canister capacity or size (such as, 300 mL or 800 mL), canister fill detection (such as, not full or full), and canister first use date/time (which can be stored in the canister memory responsive to the canister being connected to the device and/or responsive to initiation of negative pressure wound therapy).

Rate of removal of fluid from the wound can be monitored directly (for instance, by using a flow sensor) or indirectly (for instance, by monitoring the speed or duty cycle of the negative pressure source). Rate of removal of fluid can be monitored indirectly using data retrieved from the canister. In some cases rate of removal of fluid can be monitored by monitoring canister changes. Frequently changing the canister when it is full can be indicative of a higher rate of removal of fluid than infrequently changing the canister or changing the canister when it is not full. In some instances, if the rate of removal of fluid satisfies (for instance, meets and/or falls below) a fluid flow threshold (such as, around 100 mL/day), transition to a canisterless system may be suitable and could be suggested.

A determination that transition to a canisterless system is appropriate can be made when two (or more) sequential canister replacements are made, each being made over a time period that is longer than a threshold duration (for instance, three days or less or more) and each with the canister not being full. In some instances, the sequential canister replacements may need to relate to a particular canister size (such as, smaller 300 mL canister). In some implementations, an actual determination of the canister fill level can be taken into account, rather than the determination that the canister is full or not full.

In some cases, replacement of a single canister that is not full made outside of a threshold duration can trigger the determination of a transition to a canisterless system. For example, replacement of a larger canister (such as, 800 mL canister) made outside six days (or less or more) can trigger the determination. Monitoring a trend of canister changes can be used to make the determination. For instance, canister changes could be made daily and a subsequent change after three days (or less or more) or several such changes can trigger the determination.

When the canister (such as, the canister 162) is connected to the device (such as, the device 110), the canister can be checked for being included into the process for determining whether to transition to a canisterless system. The determination can include one or more of the following verifications: verifying that the canister is fresh (for instance, has not been used with another device, which can be determined by verifying that the canister memory does not already store a first use date/time), verifying that the canister is of the right size (such as, 300 mL), and verifying that the canister identification (such as, the serial number) is recognized as having been previously connected to the device. In some instances, the first two of these verifications would need to be satisfied for the canister to be included into the process for determining whether to transition to a canisterless system. The latter verification (verifying the canister as previously having been connected to the device) can be used subsequent to the initial verification that the canister should be included into the process (for instance, when the canister has been connected to the device for the first time) to overcome the issue of the process incorrectly reacting to the canister being inadvertently disconnected and then reconnected. Once the canister has been included in the process, monitoring of the frequency of canister removal and whether the canister when removed was not full (or had a fluid level equal to or below a threshold fill level) can be made.

When a 300 mL canister is not registered as being full over a course of, for instance, 3 days, the rate of removal of fluid from the wound can be assumed to be less than 100 mL/day (or 120 mL/day, 80 mL/day, 50 mL/day, or less or more). Having two such canister changes in sequence can indicate that the rate of fluid removal is less than 600 mL over the course of six days. As another example, a smaller canister can be used, such as 100 mL, and two (or more) days of not filling such canister can indicate that the rate of removal is less than 100 mL/day. Such low rate of removal can be indicative of the wound having healed sufficiently for being treated by a canisterless system. As a result, transition to a canisterless system can be suggested. The actual threshold rate of removal can be determined based on the capability of the therapy being suggested. The determination of whether to transmission to a canisterless system can be made by one or more controllers of the device (such as, the main controller 310).

Figure 13:
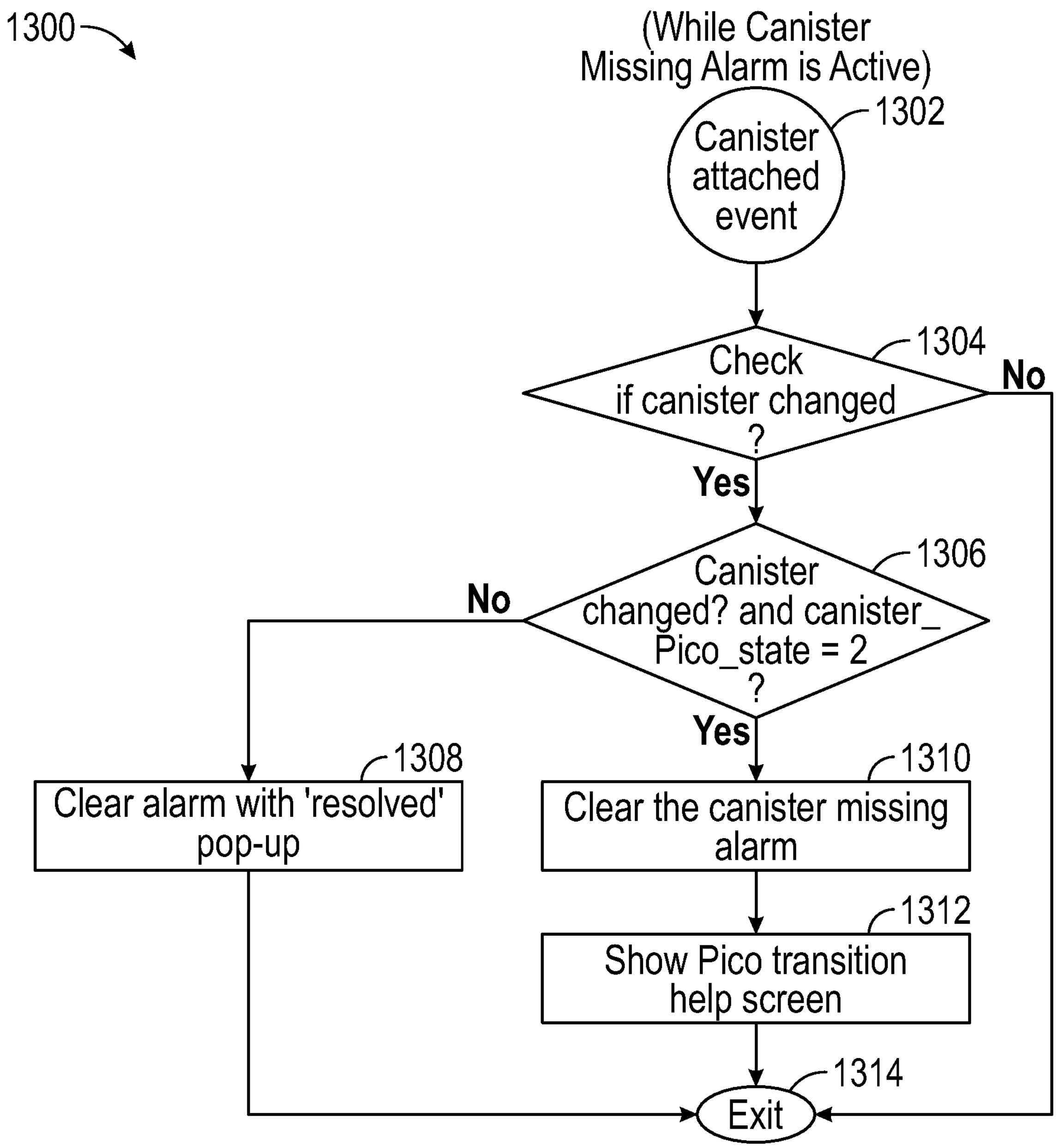
FIGS. 13 to 14 illustrate processes for transitioning to a canisterless wound therapy system.

FIG. 13 illustrates a process 1300 for transitioning to a canisterless mode. The process 1300 can be implemented by one or more controllers of the device, such as the main controller 310. The process 1300 can be executed responsive to detection that a canister has not been connected, which can be indicated by a canister missing alarm (or alert). The process 1300 can begin in block 1302 where the process can detect attachment of a new canister. The process 1300 can transition to block 1304, where it can determine if the canister was changed. This determination can be performed using any of the approaches described herein, such as that described in connection with FIG. 14. If in block 1304 the process 1300 detects that the same canister has been reattached, the process 1300 can terminate by transitioning to block 1314.

If in block 1304 the process 1300 detects that a different canister has been attached, the process can transition to block 1306 where it can determine whether the number of canister changes counted toward transitioning to a canisterless system (for instance, as described in connection with FIG. 14) satisfies a threshold. The threshold can be, for instance, two sequential canister changes. If not, the process 1300 can transition to block 1308 where it can clear the canister missing alarm, after which the process can terminate by transitioning to block 1314. If in block 1306 the process 1300 determines that the number of canister changes when the canister satisfies the threshold, the process can transition to block 1310 where it can clear the canister missing alarm. The process can subsequently transition to block 1312 where it can provide a notification that a determination of transitioning to a canisterless system has been made. Such notification is described, for example, in connection with FIG. 9. After the notification has been provided, the process 1300 can terminate by transitioning to block 1314

Figure 14:
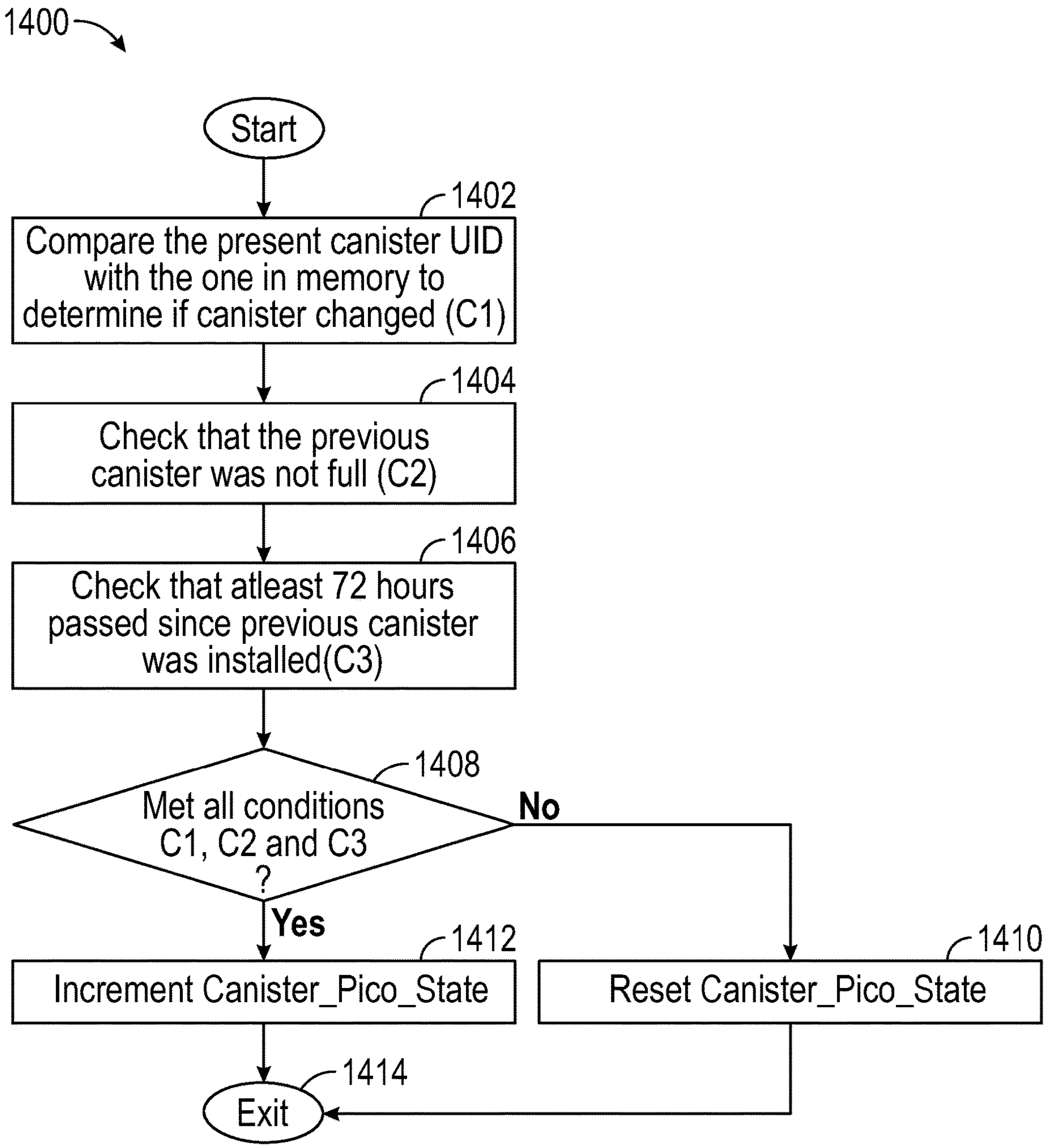

FIG. 14 illustrates a process 1400 for verifying that the canister has been changed and that the canister should be included for determining whether to transition to a canisterless system. The process 1400 can be implemented by one or more controllers of the device, such as the main controller 310. The process 1400 can be executed in block 1304 of FIG. 13.

In block 1402, the process 1400 can analyze identification of the canister that has been attached to determine whether the canister has not been previously attached to the device. In block 1404, the process 1400 can determine whether the previously attached canister (which has been replaced) was not full (or had a certain fill level). In block 1406, the process can determine whether the canister change has been performed outside of a period of time (such as, 3 days). In block 1408, the process 1400 can determine if each of the conditions in blocks 1402, 1404, and 1406 has been satisfied. If so, the process 1400 can transition to block 1412 where it can increment the number of canister changes toward transitioning to a canisterless system. This number can be utilized in block 1306 of FIG. 13. The process 1400 can subsequently terminate in block 1414. If the process 1400 determines in block 1408 that any one or more of the conditions in blocks 1402, 1404, and 1406 has not been satisfied, the process 1400 can transition to block 1410 where it can reset the number of canister changes. The process 1400 can subsequently terminate in block 1414.

Figure 9:
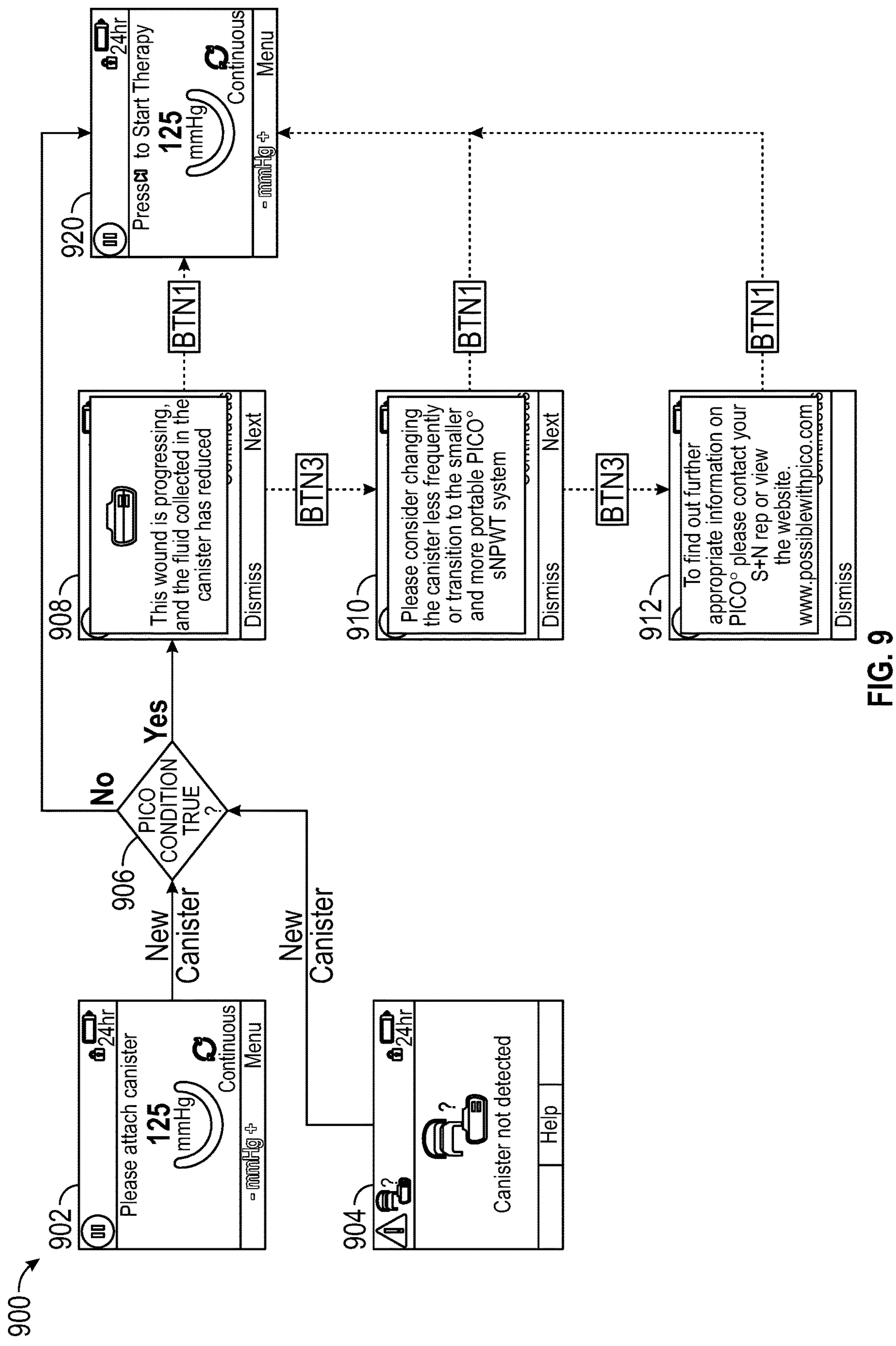
FIG. 9 illustrates a process of transitioning to a canisterless wound therapy system.

Once the determination of transitioning to a canisterless system has been made, a notification (or indication) can be provided as shown in FIG. 9, which illustrates a process 900 for transitioning to canisterless mode. The process 900 can be executed by one or more controllers of the device, such as the main controller 310. User interface screens illustrated in blocks 902, 904, 908, 910, 912, and 920 can be displayed on the display 172. Block 902 illustrates an example user interface screen for prompting the user to connect a canister. Block 904 illustrates an example user interface screen for an alarm that the canister has not been connected. Once the canister has been connected, the process can transition to block 906 where a determination regarding transitioning to a canisterless system can be made. This determination can be made using any of the approaches described herein.

If a determination for transitioning to a canisterless system is not made in block 906, the process 900 can transition to block 920, in which an example user interface screen for starting the provision of negative pressure wound therapy using a device with a canister is illustrated. If a determination for transitioning to a canisterless system is made in block 906, the process 900 can transition to block 908, in which an example user interface screen for suggesting transition to canisterless system is illustrated. As is illustrated, once the determination of transitioning to a canisterless system has been made, the transition message may not make a definite statement that the patient is suitable for the transition. Rather, the message may suggest that the HCP consider making the transition. Blocks 910 and 912 illustrate additional user interface screens for suggesting such transition. The user can advance the user interface screens from block 908 to block 910 and from block 910 to block 912 by operating one or more inputs or components on the interface panel 170. For instance, the user can press one or more buttons of the set of buttons 184.

In FIG. 9, BTIN1 corresponds to a first button of the set of buttons 184, and BTN3 corresponds to a third button of the set of buttons 184. For example, pressing the button associated with the action "Next" (such as, BTN3) can cause transition to the next block (910 or 912). The user can transition to block 920 from any of the blocks 908, 910, and 912 by pressing one of the buttons from the set of buttons 184. For example, pressing the button associated with the action "Dismiss" (such as, BTN1) can cause a transition to block 920.

In some cases, the notification can be transmitted to a remote computing device. For instance, the notification can be wirelessly transmitted to the device 334.

Advantageously, monitoring the rate of removal of fluid from the wound can be used to determine that a transition to a canisterless system could be made. Among other things, this can promote patient comfort, improve patient mobility, and increase patient's compliance with the negative pressure wound therapy.

Additional details of transitioning to a canisterless system are disclosed in U.S. Pat. No. 10,143,785 titled "Systems and Methods for Applying Reduce Pressure Therapy," U.S. Patent Publication No. 2019/0358372 titled "Negative Pressure Wound Therapy Apparatuses and Methods for Using the Same," U.S. Patent Publication No. 2021/0106735 titled "Power Source Charging for Negative Pressure Wound Therapy Apparatus," U.S. Patent Publication No. 2020/0230302 titled "Negative Pressure Wound Therapy Apparatus with Removable Panels," U.S. Patent Publication No. 2021/0106736 titled "Systems and Methods for Determining Blockages in a Negative Pressure Wound Therapy System," International Publication No. WO 2019/179943 titled "Securing Control of Settings of Wound Therapy Apparatuses," U.S. Patent Publication No. 2020/0330662 titled "Negative Pressure Wound Therapy Apparatuses and Methods of Using the Same," U.S. Patent Publication No. 2021/0038776 titled "Systems and Methods for Controlling Dual Mode Negative Pressure Wound Therapy Apparatus," and International Publication No. WO 2019/211732 titled "Exhaust Vent for a Negative Pressure Wound Therapy System," each of which is incorporated by reference in its entirety.

While certain examples are presented in the context of transitioning to a canisterless negative pressure wound therapy system, approaches described herein are generally applicable to determining (and suggesting) a transition from a first treatment system to a second treatment system that is different from the first treatment system. The first treatment system can be a less transportable, larger, and heavier system. The second treatment system can be a more transportable, smaller, and lighter system. In some cases, the first treatment system can be a high-exudate rate (or high-exudate) negative pressure wound therapy system and the second treatment system can be a low-exudate rate (or low-exudate) negative pressure wound therapy system (such as, one or more of a canisterless system, mechanically-powered system, small system with a canister, or the like).

Multiparameter PID Control

Negative pressure wound therapy systems may need to be able to maintain the desired pressure setpoint over a large variety of operating conditions, accounting for one or more of internal device variations (such as, voltage or pump-to-pump variation), external environmental variations (such as, temperature or atmospheric pressure), a variety of user-selectable pressure setpoints, wound conditions (such as, wound volume, dressing air leak, or exudate volume and viscosity). Such variations can make it difficult to design a system that uses a fixed drive signal for controlling the negative pressure source (such as, a drive signal applied to the motor or another actuator of the negative pressure source). In some cases, a proportional-integral-derivative (PID) control loop (sometimes referred to as PID loop) can be used. The PID loop may need to be stable and yet responsive over all conditions in which the system operates (such as, the one or more variations described herein).

A PID loop can have a fixed set of parameters that control the gains inside the loop. Such parameters can include:

- Proportional Gain (P-gain) that can be used to drive the PID loop output based upon a ratio of the output error (such as, the difference between the current pressure compared to the target pressure)
- Integral Gain (I-gain) that can be used to drive the PID loop output based upon a ratio of the system integral error (such as, the sum of the current and all previous output errors)
- Differential Gain (D-gain) that can be used to drive the PID loop output based upon a ratio of the difference between the current output error and the previous error In some cases, a negative pressure wound therapy system can implement the proportional gain and integral gain, but not the differential gain. Such control loop is sometimes referred to as a PI loop (which can be a special case of a PID loop).

The proportional gain can be more important that the other gains and may account for the main drive when the output error is very large. The integral gain can correct steady state errors once the system has mostly reached the target pressure. The differential gain can handle acceleration/deceleration toward the target pressure and may account for inertia in the system.

A single set of PID parameters can be used to control a symmetrical system. An example of a symmetrical system is driving a pointer to a target angle (such as, a speedometer needle). In such system, correction of the output requires the same drive regardless of the target position. However, a negative pressure wound therapy system may not be symmetrical for at least the following reasons. First, establishing a higher negative pressure level setpoint (or higher level of vacuum) may take more power than establishing lower negative pressure level setpoint. For instance, the power needed to reduce pressure from 0 mmHg to −50 mmHg is much less than that needed to reduce pressure from −150 mmHg to −200 mmHg, even though the error in both cases is 50 mmHg. This may be due to the following: the flow rate in the fluid flow path can increase as the negative pressure increases (or becomes more negative), which can cause a proportional squared increase in the negative pressure source power and the extra pressure on the negative pressure source components increases the power required to maintain higher negative pressures. Second, the system may be able to drive the negative pressure source only in one direction (such as, to reduce pressure but not increase it). If the negative pressure overshoots, then the drive signal for controlling the negative pressure source is turned off, and the system would need to wait until the negative pressure naturally decays due to, for example, one or more leaks in the fluid flow path.

Accordingly, in some instances, a PID loop which is optimized for good performance for a target setpoint of, for instance, −200 mmHg would not perform as well for a target setpoint of, for example, −50 mmHg. The reason can be seen in the examination of the proportional gain (P-gain). If the system is in the initial state (such as, when the fluid flow path is at atmospheric pressure) and the target setpoint is −200 mmHg, the initial error is −200. Assuming a P-gain of −1, to convert the error into a fractional power for driving the negative pressure source (which may be expressed in percentages), means that the PID loop would initially attempt to drive the negative pressure source at 200% (which can be determined using the equation (error*P-gain), which would correspond to −200*1=200%). Since the negative pressure source can be driven at a maximum of 100%, the negative pressure source would continue to be driven at 100% until pressure in the fluid flow path reaches, for instance, −100 mmHg. At this point, the proportional gain may reduce the fractional drive power linearly (since the error has decreased) until the target setpoint is achieved. Suppose that the target setpoint is −25 mmHg and the same P-gain of −1 is used. The initial error is −25, and only 25% of negative pressure source power would be applied (−25*−1=25%). As a result, the system would be very slow to reach the target setpoint. This may be due to the negative pressure source having to overcome a fixed volume of gas (such as, air) in the system that needs to be evacuated before any negative pressure value can be achieved in the fluid flow path.

Suppose that the system is optimized to reduce pressure to −25 mmHg. A much higher P-gain could be selected, such as −8, since the expected error would be smaller. This would allow for an initial negative pressure source power of 100% at start-up (−25*−8=200%, which would be limited to 100%). The power would be reduced linearly towards the target pressure. However, if P-gain value of −8 is applied to the system to reduce pressure to −200 mmHg, the PID loop would attempt to drive the negative pressure source at 1600% (−200*8). This would be limited to 100% for the majority of the duration of time of driving the negative pressure source to establish the setpoint, only reducing to a drive below 100% very close to the target pressure. Undesirably, the inertia of the system would likely cause a large overshoot of the target pressure.

Figure 12:
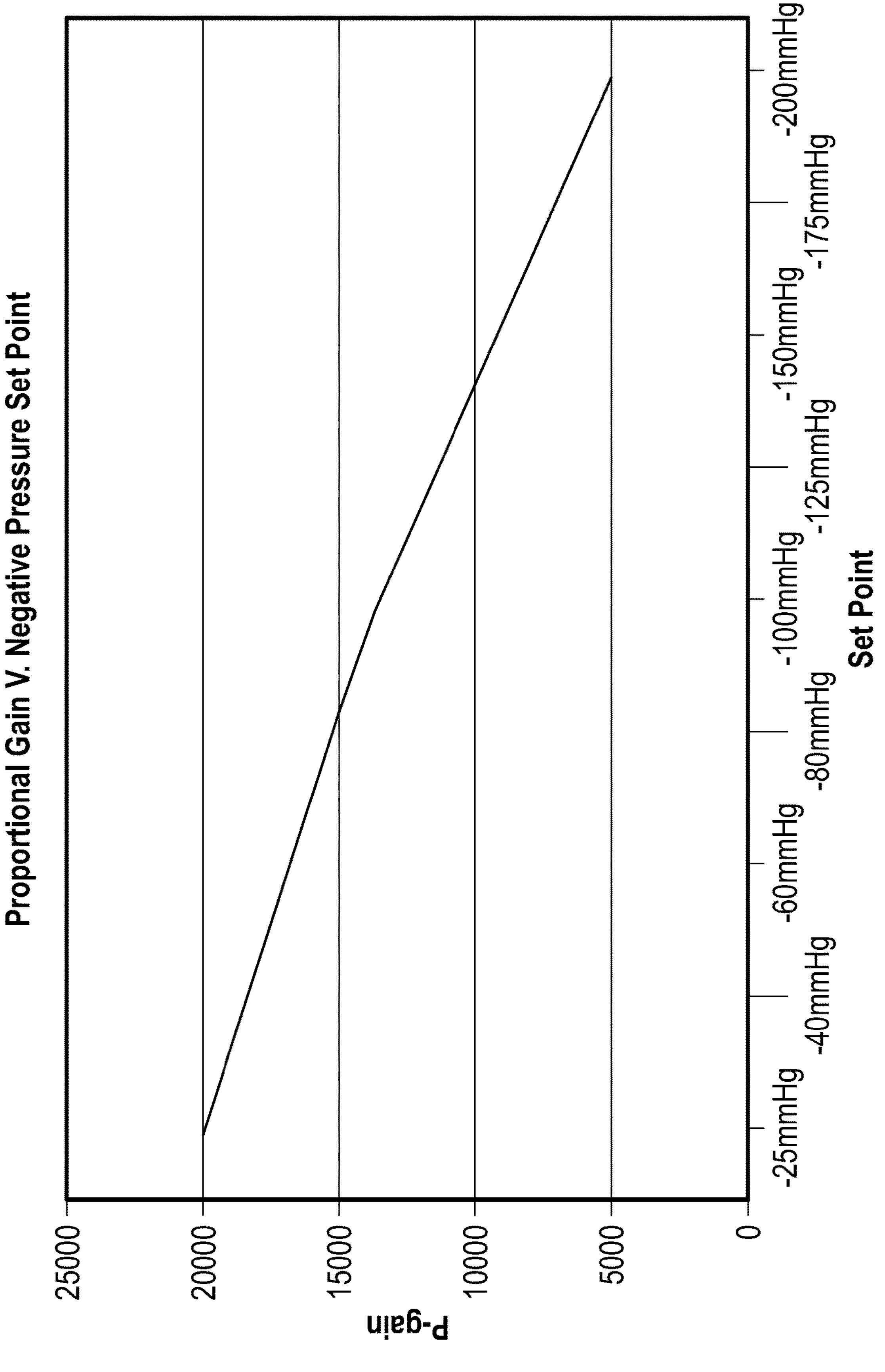
FIG. 12 illustrates a plot of proportional gain versus target pressure.

To address these problems, individual PID loop parameters for each target pressure setpoint can be used. In some cases, different P-gain, I-gain, or D-gain values can be determined for one or more different negative pressure setpoints. For instance, different P-gain and I-gain values can be determined for each negative pressure setpoint (or for at least some different setpoints) when PI loop is being used. The ratio of P-gain to I-gain can be about 0.1 (or 1%). P-gain values can be linearly proportional to the setpoint, as is illustrated in FIG. 12. Using such P-gain and I-gain values can result in the PID loop providing good control at both high and low pressures. Target pressure can be achieved in a reasonable time without producing any large overshoots.

For example, the following P-gain and I-gain values for each negative pressure setpoint can be determined (for instance, via testing) and used for PI loop:

| Target Pressure | P-gain | I-gain |
|---|---|---|
| −25 mmHg | 20000 | 20 |
| −40 mmHg | 18700 | 19 |
| −60 mmHg | 17000 | 17 |
| −80 mmHg | 15300 | 15 |
| −100 mmHg | 13600 | 14 |
| −125 mmHg | 11400 | 11 |
| −150 mmHg | 9300 | 9 |
| −175 mmHg | 7100 | 7 |
| −200 mmHg | 5000 | 5 |

In some cases, instead of a linear relationship between the P-gain and the setpoint (such as, in the table above and in FIG. 12), a squared relationship could be used. Such relationship may model the pressure to power curve more closely. In some instances, a line fitting or curve fitting can be used. Such approaches may further account for the asymmetrical nature of the negative pressure wound therapy system.

To compensate for the asymmetrical nature of the negative pressure wound therapy system, the I-gain can be adjusted when pressure in the fluid flow path is above the setpoint (or is more negative than the setpoint). This can reduce the size and duration of any overshoot. The adjustment factor can be a constant, for instance, an integer value (such as, 2, 3, 5, or more than 5). The adjustment can be a multiplication (in such case, the adjustment factor can be referred to as a multiplier). For example, assume that the setpoint is −125 mmHg and the multiplier is M. If the actual pressure in the fluid flow path is below the setpoint (or more positive than −125 mmHg), the I-gain used to bring the actual pressure to the target can be X (which may be an integer value). If the actual pressure is above the setpoint (or is more negative than −125 mmHg), the I-gain can be adjusted by the multiplier to be M*X. This can reduce any overshoots and, as result, reduce the risk of providing too much negative pressure to the patient, which may cause discomfort or pain.

Adjustment of the I-gain can be performed after the setpoint has been achieved to reduce the size and duration of any pressure overshoots, which reduces the risk of overpressurizing the wound. In some cases, adjustment of the I-gain can be performed before the setpoint has been achieved to facilitate achieving the target pressure faster (which may carry the risk of causing pressure overshoots).

If the multiplier is selected as being too large, this may collapse the integral term (or the integral sum) of PI or PID loop too quickly even on slight pressure variations that may naturally occur, for instance, due to bubbles of exudate being aspirated and causing slight disturbances in the pressure in the fluid flow path. Using a multiplier that is too large can produce an uneven and undesirable pressure regulation with cyclical drops in the drive signal power.

PID (or PI) loop can be performed by one or more controllers, such as the pump controller 370. P-gain values and I-gain values for different setpoints can be stored in memory, such as memory 350. For instance, a lookup table indexed by the setpoint can be used.

In some cases, pressure at the wound can be measured directly, for instance, by one or more pressure sensors positioned at or near the wound. In such cases, references to pressure in the fluid flow path used in this section can be replaced with pressure at the wound.

Advantageously, the approaches described in this section can facilitate good control of the negative pressure source at both high and low negative pressure setpoints. Target pressure can be achieved quickly and without any large overshoots.

Tutorial for Operating a Negative Pressure Wound Therapy Device

Any of the negative pressure wound therapy devices disclosed herein (such as, device 110) can be configured to provide one or more tutorials for operating the device. The one or more tutorials can be provided in AV format. For example, one or more tutorials can be selected from a user interface displayed on the display 172. The one or more tutorials can include device overview, applying negative pressure wound therapy, resolving alarms, or the like. One or more controllers (such as, the main controller 310) can control the provision of one or more tutorials.

As described herein, the device can include a user interface (such as, the interface 170) for operating the device. The user interface can include one or more indicators 174 or one or more controls or buttons (including, for example and without limitation, a therapy start and pause button 180 or an alarm/alert mute button 182 and one or more input controls or buttons 184). To further facilitate the user's learning of how to operate the device, one or more user interface components that the user would need to operate to cause the device to perform a particular function can be emphasized (such as, illuminated) while the one or more tutorials are being provided.

Figure 10A:
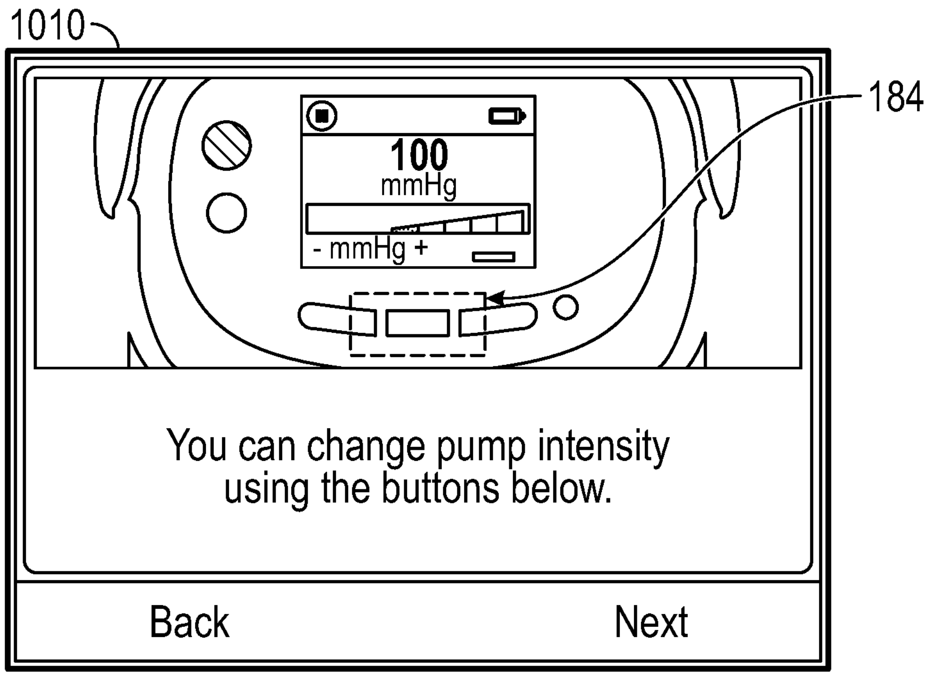
FIGS. 10 to 11 provide graphical user interface screens.
Figure 10B:
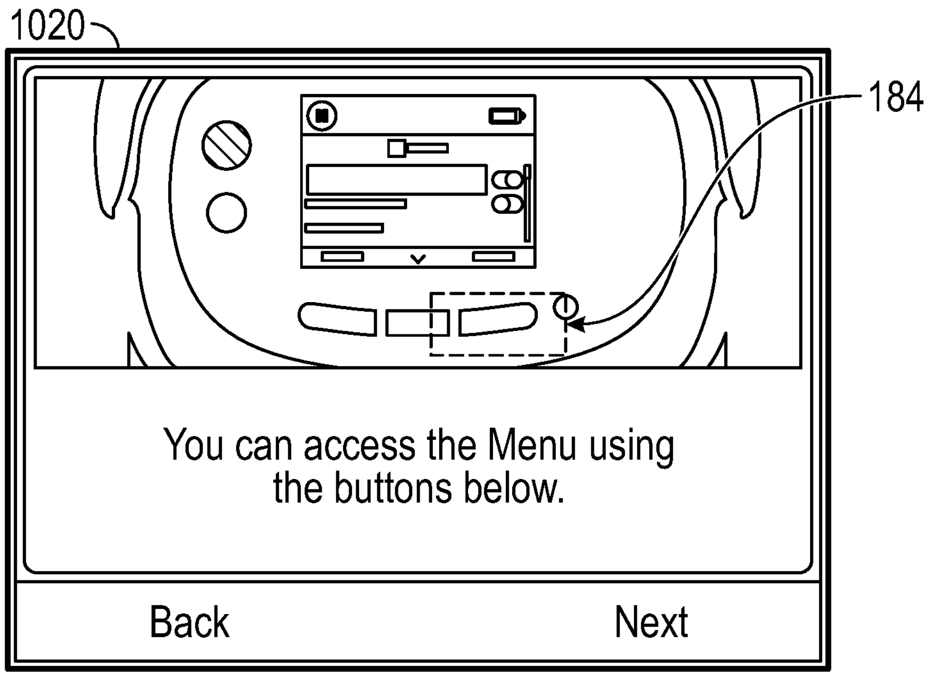

For instance, with reference to a user interface screen 1010 illustrated in FIG. 10A, one (or more than one) of the buttons 184 can be used to change the intensity of negative pressure wound therapy. The user interface screen 1010 can be displayed on the display 172. While the user interface screen 1010 is being displayed, the relevant button 184 can be illuminated (or otherwise highlighted to the user). As another example, with reference to a user interface screen 1020 illustrated in FIG. 10B, one of the buttons 184 can be used to access a menu on the display 172. While the user interface screen 1020 is being displayed on the display 172, the relevant button 184 can be illuminated (or otherwise highlighted to the user).

Figure 10C:
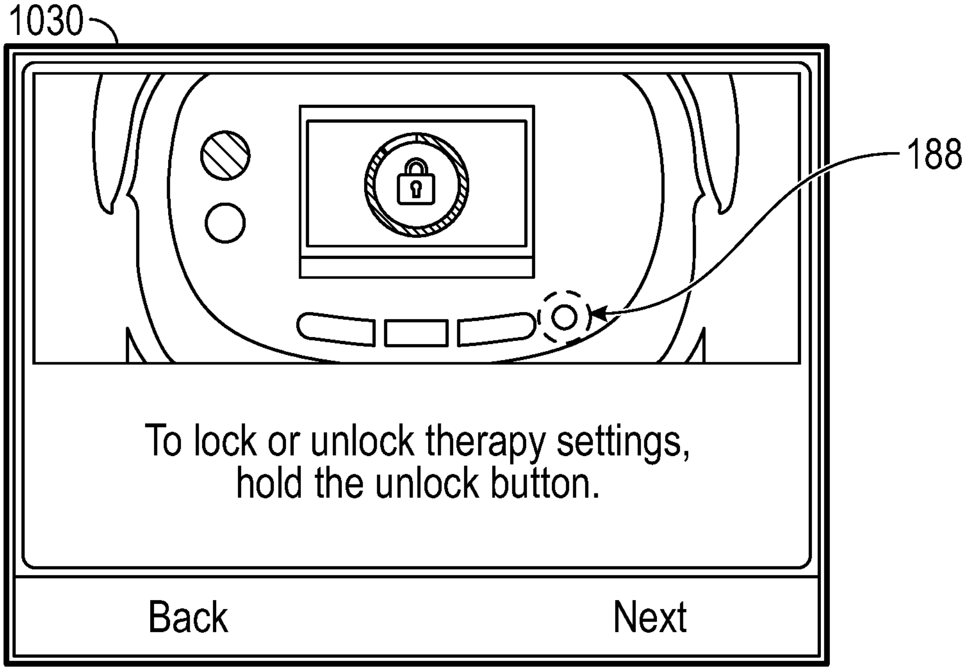
Figure 10D:
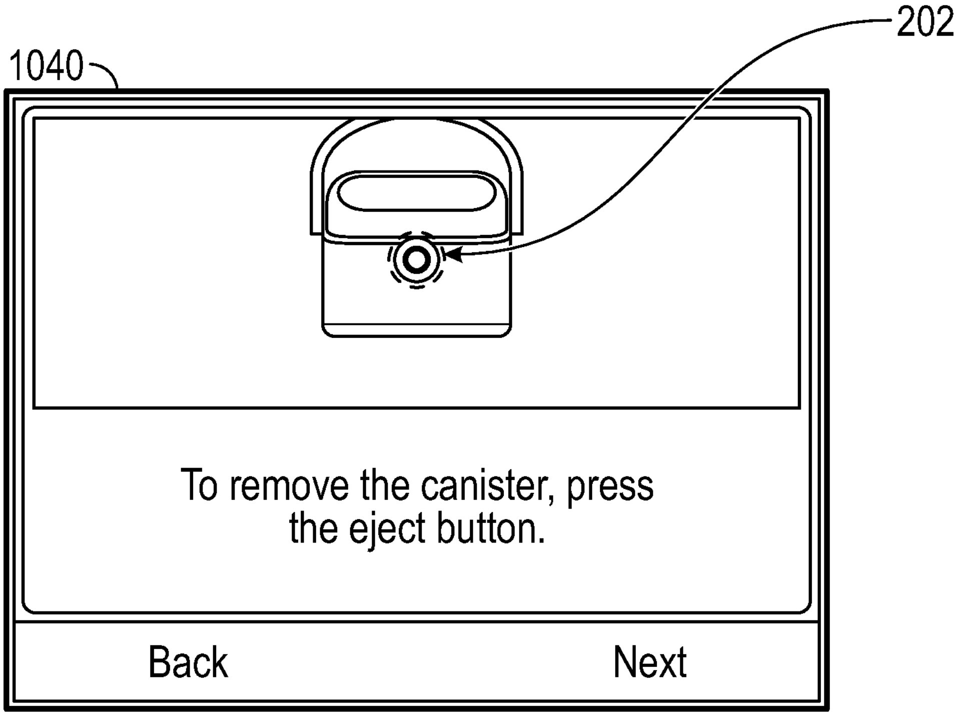

As yet another example, with reference to a user interface screen 1030 illustrated in FIG. 10C, the button 188 can be operated to lock or unlock the functionality of various other controls (for instance, one or more buttons for adjusting therapy settings). While the user interface screen 1030 is being displayed, the button 188 can be illuminated (or otherwise highlighted to the user). As yet another example, with reference to a user interface screen 1040 illustrated in FIG. 10D, the button 202 can be operated to disconnect and remove the canister. While the user interface screen 1040 is being displayed, the button 202 can be illuminated (or otherwise highlighted to the user). Similarly, the start and pause button 180 can be illuminated (or otherwise highlighted to the user).

Therapy Summary and Logs

Any of the negative pressure wound therapy devices disclosed herein (such as, device 110) can be configured to record data related to the provision of therapy and provide one or more summaries to the user. For example, the one or more summaries can be displayed on the display 172. One or more controllers (such as, the main controller 310) can control the recording of data and providing the one or more summaries.

Figure 11A:
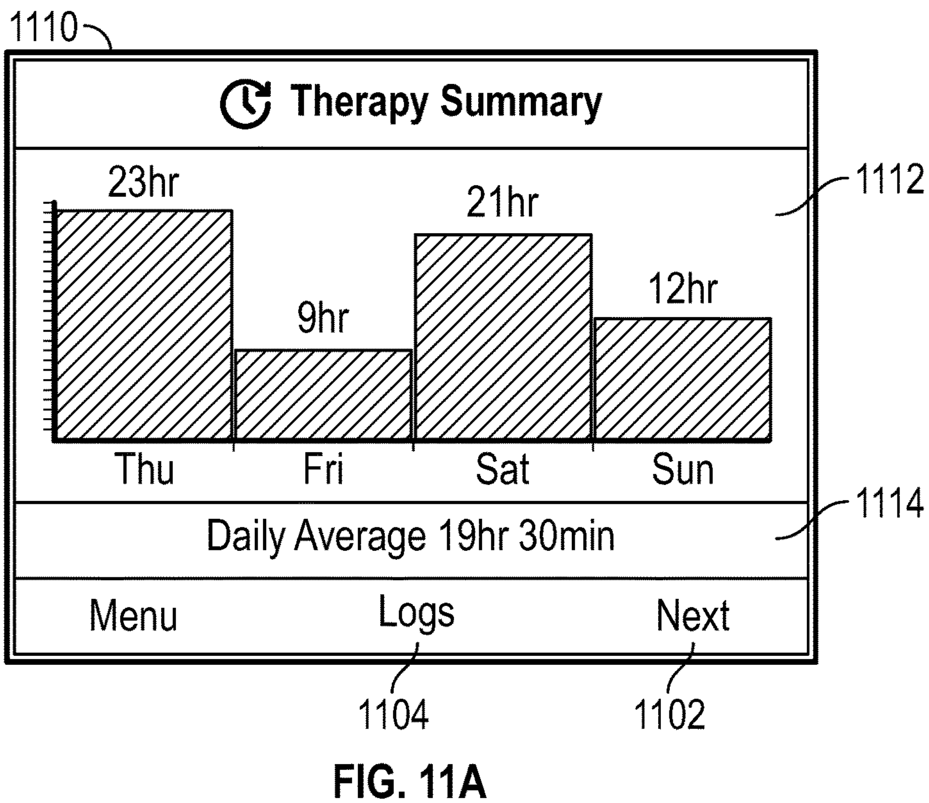

FIG. 11A illustrates a user interface screen 1110 that provides a therapy summary for several days of therapy. The screen 1110 can include a bar graph 1112 illustrating therapy hours for the several days captured by the summary. The several days can include the present day (which in the illustrated example can be a Sunday) and three preceding days (such as, Saturday, Friday, and Thursday). In some implementations, formats other than or in addition to bar graph 1112 can be displayed (such as, a pie graph, line graph, or the like). The user interface screen 1110 can include a daily average 1114 determined for the several days (such as, four days in the illustrated example).

Figure 11B:
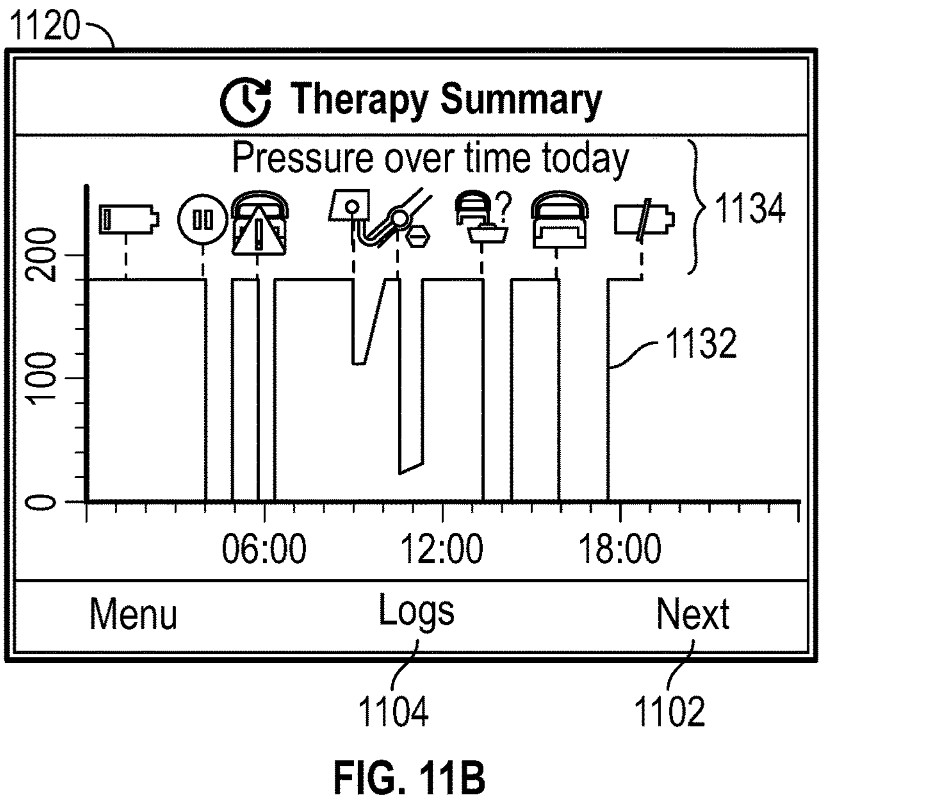

FIG. 11B illustrates a user interface screen 1120 that provides a therapy summary for a particular day (which can correspond to the present day, such as Sunday). The therapy summary of the screen 1120 can be more detailed than the summary in the screen 1110. The user interface screen 1120 can be accessed from the screen 1110 by selecting the option 1102 (labeled "Next") in FIG. 11A. As described herein, option 1102 can be activated by one of the buttons 184. The user interface screen 1120 can illustrate a graph 1132 of negative pressure levels over time for the particular day. Various alarms or other events 1134 can be illustrated, and can be positioned to coincide with the time of occurrence. This can facilitate the user's analysis and understanding of how negative pressure wound therapy had been provided for the particular day.

Figure 11C:
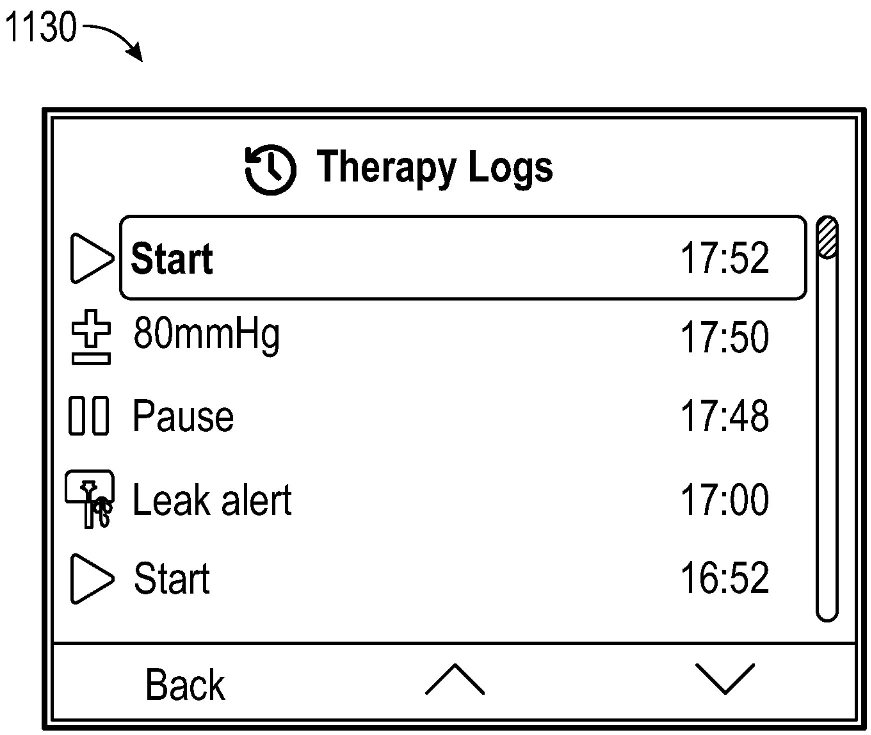

Selecting the option 1104 (labeled "Logs") in FIG. 11B (or FIG. 11A) can bring up a user interface screen 1130 shown in FIG. 11C. As described herein, option 1104 can be activated by one of the buttons 184. The user interface screen 1130 can provide a more detailed list of the various alarms or other events 1134. As is illustrated, times of occurrence of the various alarms or other events 1134 can be provided.

Figure 11D:
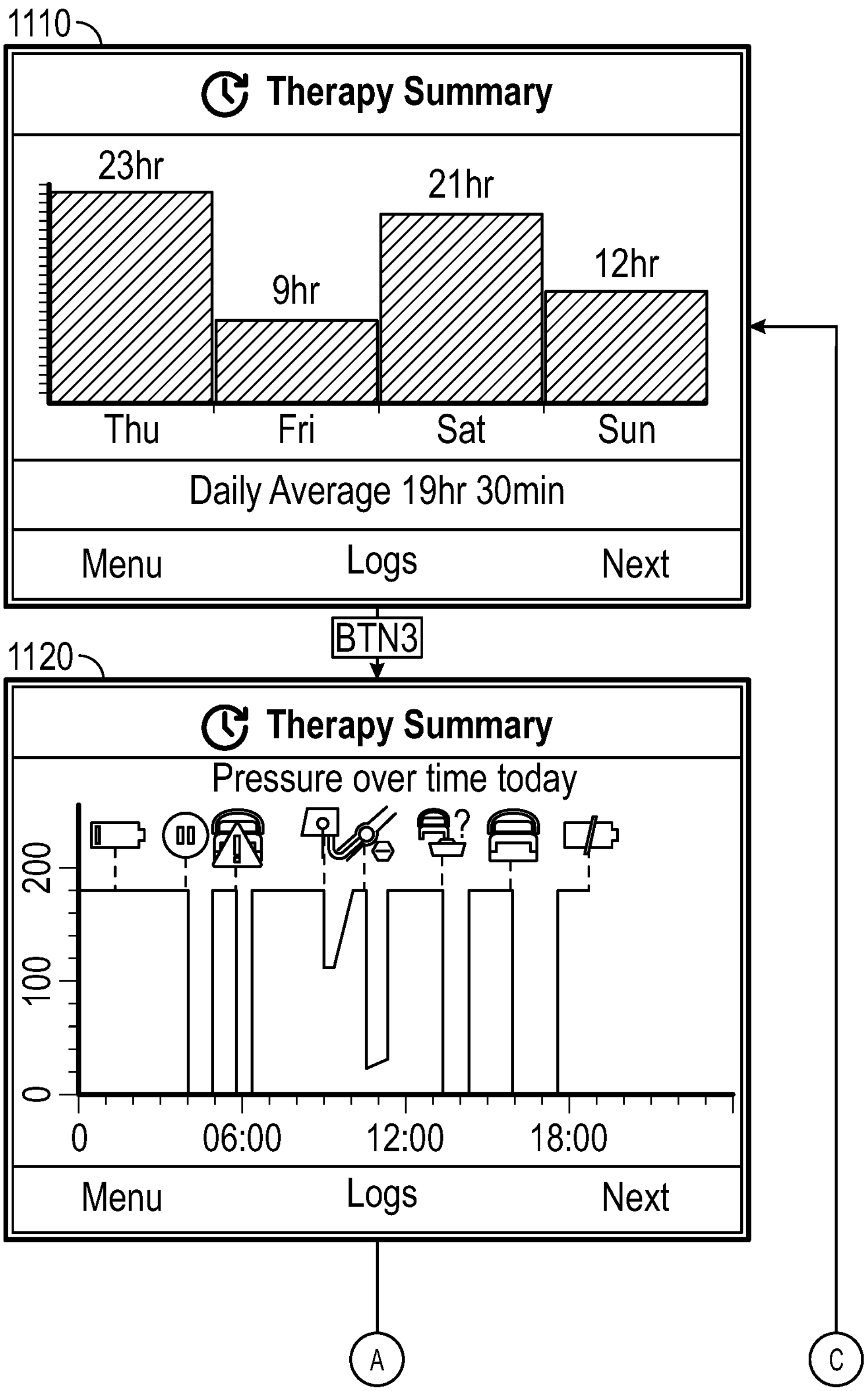
Figure 11D:
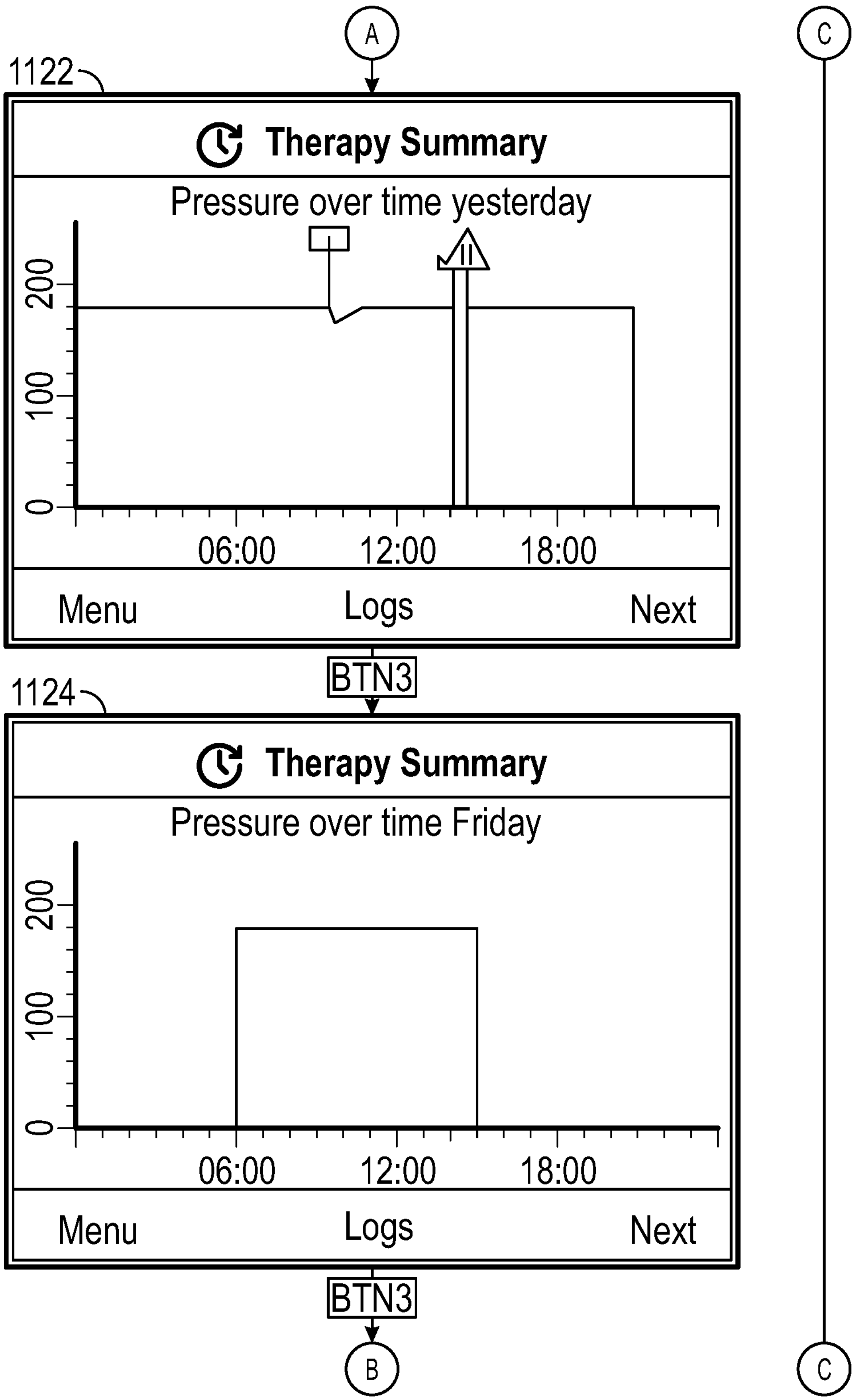
Figure 11D:
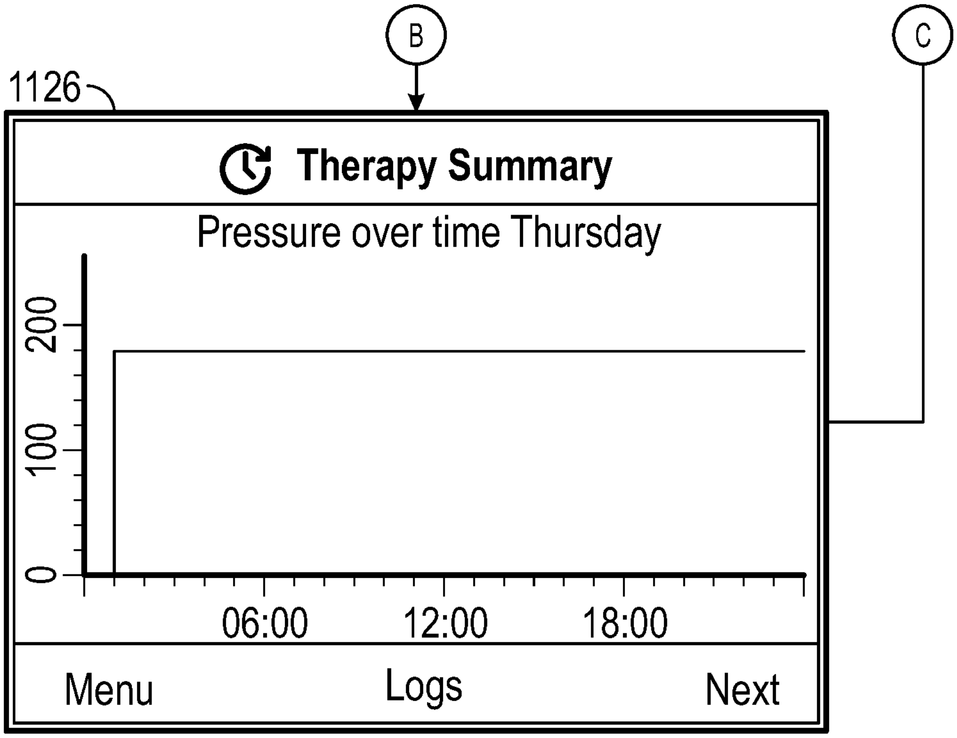

FIG. 11D illustrates a transition among therapy summaries for the several days illustrated in FIG. 11A (such as, four days Sunday, Saturday, Friday, and Thursday). The transition can begin with the user interface screen 1110 that provides the therapy summary for the several days. Selecting the option 1102 (labeled "Next") on the screen 1110 can bring up the user interface screen 1120 that provides a more detailed therapy summary for the present day (such as, Sunday). Selecting the option 1102 (labeled "Next") on the screen 1120 can bring up a user interface screen 1122 that provides a more detailed therapy summary for the previous day (such as, Saturday). Selecting the option 1102 (labeled "Next") on the screen 1122 can bring up a user interface screen 1124 that provides a more detailed therapy summary for the day before yesterday day (such as, Friday). Finally, selecting the option 1102 (labeled "Next") on the screen 1124 can bring up a user interface screen 1126 that provides a more detailed therapy summary from three days ago (such as, Thursday). User interface screens 1122, 1124, and 1126 can be similar to the user interface screen 1120. Selecting the option 1102 (labeled "Next") on the screen 1126 can bring up the user interface screen 1110 that provides the therapy summary for the several days.

Advantageously, the approaches described in this section can provide data related to provision of therapy in a user friendly and easy to understand format.

Inhibiting Delivery of Negative Pressure Wound Therapy

In some cases, delivery of negative pressure can be inhibited by any of the pump assemblies disclosed herein (such as, the pump assembly 160) responsive to detecting one or more operating conditions. For example, delivery of negative pressure can be inhibited responsive to detecting that one or more canister filters are occluded with fluid. While the canister can include one or more hydrophobic filters that inhibit passage of liquid into the pump assembly 160, continuous application of negative pressure (particularly at a higher negative pressure set point, such as about −200 mmHg) when the canister is completely filled with fluid and occluding more filters become occluded can mechanically stress one or more filter membranes and cause a mechanical failure of the one or more filters (such as, tearing or detachment). As a result, there may be a risk of damaging the pump assembly 160 with liquid. To mitigate this risk, it can be advantageous to inhibit the delivery of negative pressure (such as, by deactivating the negative pressure source) responsive to detecting that the one or more filters are occluded.

Detection of occlusion of the one or more filters can be performed as follows. The pump assembly 160 (for example, via one or more controllers 310 or 370) may not be configured to directly detect occlusion of the one or more filters. In some cases, this can be performed indirectly in response to detecting that the canister is full and there is a blockage in the fluid flow path. These two conditions may be independently detected by the pump assembly 160, for instance, to distinguish between a blockage due to the canister being full (proximal blockage) and a blockage upstream of the canister (distal blockage). Detection of both of these conditions can imply that the one or more filters are occluded since both proximal and distal blockages have been detected. Delivery of negative pressure can be inhibited responsive to detecting that the canister is full and there is a blockage in the fluid flow path.

In some implementations, canister full detection can be performed by detecting fluid connection using two electrodes placed inside the canister. Additional details of canister full detection are disclosed in International Patent Application No. PCT/EP2022/060463, filed on Apr. 20, 2022, and titled "Canister Status Determination for Negative Pressure Wound Therapy Devices," which is incorporated by reference in its entirety. Blockage detection can be performed by monitoring the activity of the negative pressure source (for instance, by monitoring the speed of a motor of the negative pressure source, monitoring the duty cycle of an actuator of the negative pressure source, or the like) and comparing the activity to one or more activity thresholds indicative of a blockage in the fluid flow path. Additional details of blockage detection are disclosed in U.S. Pat. No. 9,737,649, issued on Aug. 22, 2017 and titled "Systems and Methods for Applying Reduced Pressure Therapy" and U.S. Pat. No. 10,744,239, issued on Aug. 18, 2020 and titled "Leak Detection in Negative Pressure Wound Therapy System," each of which is incorporated by reference in its entirety.

Delivery of negative pressure can be restarted responsive to clearing at least one of canister full or blockage in the fluid flow path. While blockage is unlikely to clear due to the negative pressure source being deactivated, canister full may clear if canister full detection was triggered as a result of an incorrect orientation of the pump assembly 160 (rather than due to the canister being full). For example, the pump assembly 160 may have been tilted or placed upside down, which triggered canister full detection. Placing the pump assembly 160 in an upright position may clear the canister full condition, thereby allowing the delivery of negative pressure wound therapy to continue.

Other Variations

Any of the negative pressure wound therapy systems and/or devices disclosed herein can implement any combination of features disclosed in various foregoing sections. For example, any of the systems and/or devices can implement any combination of approaches described in one or more of: “Fall Detection and Device Orientation Detection” section, “Transitioning to a Different Therapy System” section, “Multiparameter PID Control” section, “Tutorial for Operating a Negative Pressure Wound Therapy Device” section, “Therapy Summary and Logs,” or “Inhibiting Delivery of Negative Pressure Wound Therapy” section.

Although some embodiments describe negative pressure wound therapy, the systems, devices, and/or methods disclosed herein can be applied to other types of therapies usable standalone or in addition to TNP therapy. Systems, devices, and/or methods disclosed herein can be extended to any medical device, and in particular any wound treatment device. For example, systems, devices, and/or methods disclosed herein can be used with devices that provide one or more of ultrasound therapy, oxygen therapy, neurostimulation, microwave therapy, active agents, antibiotics, antimicrobials, or the like. Such devices can in addition provide TNP therapy. The systems and methods disclosed herein are not limited to medical devices and can be utilized by any electronic device.

Any of transmission of data described herein can be performed securely. For example, one or more of encryption, https protocol, secure VPN connection, error checking, confirmation of delivery, or the like can be utilized.

Although some embodiments describe the use of accelerometer(s) and accelerometer data, any other motion sensor(s) can be used. For example, one or more shock or impact sensors can be utilized.

Any value of a threshold, limit, duration, etc. provided herein is not intended to be absolute and, thereby, can be approximate. In addition, any threshold, limit, duration, etc. provided herein can be fixed or varied either automatically or by a user. Furthermore, as is used herein relative terminology such as exceeds, greater than, less than, etc. in relation to a reference value is intended to also encompass being equal to the reference value. For example, exceeding a reference value that is positive can encompass being equal to or greater than the reference value. In addition, as is used herein relative terminology such as exceeds, greater than, less than, etc. in relation to a reference value is intended to also encompass an inverse of the disclosed relationship, such as below, less than, greater than, etc. in relations to the reference value.

Features, materials, characteristics, or groups described in conjunction with a particular aspect, embodiment, or example are to be understood to be applicable to any other aspect, embodiment or example described herein unless incompatible therewith. All of the features disclosed in this specification (including any accompanying claims, abstract and drawings), and/or all of the steps of any method or process so disclosed, can be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated and/or disclosed may differ from those shown in the figures. Depending on the embodiment, certain of the steps described above may be removed, others may be added. For example, the actual steps and/or order of steps taken in the disclosed processes may differ from those shown in the figure. Depending on the embodiment, certain of the steps described above may be removed, others may be added. For instance, the various components illustrated in the figures or described herein may be implemented as software and/or firmware on a processor, controller, ASIC, FPGA, and/or dedicated hardware. The software or firmware can include instructions stored in a non-transitory computer-readable memory. The instructions can be executed by a processor, controller, ASIC, FPGA, or dedicated hardware. Hardware components, such as controllers, processors, ASICs, FPGAs, and the like, can include logic circuitry. Furthermore, the features and attributes of the specific embodiments disclosed above may be combined in different ways to form additional embodiments, all of which fall within the scope of the present disclosure.

User interface screens illustrated and described herein can include additional and/or alternative components. These components can include menus, lists, buttons, text boxes, labels, radio buttons, scroll bars, sliders, checkboxes, combo boxes, status bars, dialog boxes, windows, and the like. User interface screens can include additional and/or alternative information. Components can be arranged, grouped, displayed in any suitable order.

Conditional language used herein, such as, among others, “can,” “could”, “might,” “may,” “e.g.,” and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment. The terms “comprising,” “including,” “having,” and the like are synonymous and are used inclusively, in an open-ended fashion, and do not exclude additional elements, features, acts, operations, and so forth. Also, the term “or” is used in its inclusive sense (and not in its exclusive sense) so that when used, for example, to connect a list of elements, the term “or” means one, some, or all of the elements in the list. Further, the term “each,” as used herein, in addition to having its ordinary meaning, can mean any subset of a set of elements to which the term “each” is applied. Additionally, the words “herein,” “above,”

"below," and words of similar import, when used in this application, refer to this application as a whole and not to any particular portions of this application.

Conjunctive language, such as the phrase "at least one of X, Y and Z," unless specifically stated otherwise, is to be understood with the context as used in general to convey that an item, term, etc. may be either X, Y, or Z, or a combination thereof. Thus, such conjunctive language is not generally intended to imply that certain embodiments require at least one of X, at least one of Y and at least one of Z to each be present.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations.

Although the present disclosure includes certain embodiments, examples and applications, it will be understood by those skilled in the art that the present disclosure extends beyond the specifically disclosed embodiments to other alternative embodiments and/or uses and obvious modifications and equivalents thereof, including embodiments which do not provide all of the features and advantages set forth herein. Accordingly, the scope of the present disclosure is not intended to be limited by the specific disclosures of preferred embodiments herein, and may be defined by claims as presented herein or as presented in the future.

What is claimed is:

1. A negative pressure wound therapy device comprising:
- a housing;
- a negative pressure source supported by the housing and configured to be connected, via a fluid flow path, to a wound covered by a wound dressing, the negative pressure source further configured to provide negative pressure to the wound; and
- an electronic circuitry supported by the housing, the electronic circuitry configured to detect motion of the housing and further configured to:
  - based on the motion of the housing, detect that the housing is falling and determine a duration of a fall; and
  - provide a first indication responsive to determining that the duration of the fall satisfies a duration threshold.

2. The negative pressure wound therapy device of claim 1, wherein the electronic circuitry comprises an accelerometer, and wherein the electronic circuitry is configured to detect that the housing is falling responsive to determining that an acceleration detected by the accelerometer satisfies a first acceleration threshold indicative of low acceleration.

3. The negative pressure wound therapy device of claim 2, wherein the acceleration detected by the accelerometer comprises one or more of acceleration along a z-axis or a magnitude of acceleration along multiple axes.

4. The negative pressure wound therapy device of claim 2, wherein the electronic circuitry is configured to determine the duration of the fall responsive to detecting a duration of time during which the acceleration detected by the accelerometer satisfies the first acceleration threshold.

5. The negative pressure wound therapy device of claim 2, wherein the electronic circuitry is configured to:
- determine a first time at which the acceleration detected by the accelerometer initially satisfies the first acceleration threshold;
- determine a second time at which the housing makes a first impact with a surface; and
- determine the duration of the fall based on a time difference between the second time and the first time, wherein determining the duration of the fall is based on the time difference and accounts for a possible rotation of the housing during the fall.

6. The negative pressure wound therapy device of claim 5, wherein the electronic circuitry is configured to determine the second time responsive to detecting that the acceleration detected by the accelerometer satisfies a second acceleration threshold indicative of high acceleration.

7. The negative pressure wound therapy device of claim 1, further comprising an electronic control circuitry configured to operate the negative pressure source, wherein the electronic circuitry is configured to cause the electronic control circuitry to transition from a non-operational state to an operational state responsive to determining that the duration of the fall satisfies the duration threshold.

8. The negative pressure wound therapy device of claim 1, wherein the electronic circuitry is further configured to determine a height of the fall based on the duration of the fall.

9. The negative pressure wound therapy device of claim 1, wherein the first indication comprises one or more of deactivating the negative pressure source or performing one or more tests of the negative pressure wound therapy device.

10. The negative pressure wound therapy device of claim 1, wherein the electronic circuitry is further configured to, based on the motion of the housing, detect that the housing is tilted and provide a second indication responsive to detecting that the housing is tilted.

11. The negative pressure wound therapy device of claim 10, wherein the electronic circuitry comprises an accelerometer, and wherein the electronic circuitry is configured to detect that the housing is tilted responsive to determining that an acceleration detected by the accelerometer satisfies a tilt threshold.

12. The negative pressure wound therapy device of claim 11, wherein the acceleration comprises acceleration along a z-axis.

13. The negative pressure wound therapy device of claim 11, wherein the second indication comprises deactivating the negative pressure source.

14. A method of operating a negative pressure wound therapy device, the method comprising:
- detecting a motion of a housing of the negative pressure wound therapy device, the housing supporting an electronic circuitry and a negative pressure source configured to be connected, via a fluid flow path, to a wound covered by a wound dressing and further configured to provide negative pressure to the wound; and at a first time:

based on the motion of the housing, detecting that the housing is falling and determining a duration of a fall; and providing a first indication responsive to determining that the duration of the fall satisfies a duration threshold, wherein the method is performed under control of the electronic circuitry.

15. The method of claim 14, wherein detecting that the housing is falling is performed responsive to determining that an acceleration satisfies a first acceleration threshold indicative of low acceleration.

16. The method of claim 15, wherein determining the duration of the fall is performed responsive to detecting a duration of time during which the acceleration satisfies the first acceleration threshold.

17. The method of claim 15, further comprising:

determining an initial time at which the acceleration initially satisfies the first acceleration threshold;

responsive to detecting that the acceleration satisfies a second acceleration threshold indicative of high acceleration, determining an impact time at which the housing makes a first impact with a surface; and determining the duration of the fall based on a time difference between the impact time and the initial time, wherein determining the duration of the fall is based on the time difference and accounts for a possible rotation of the housing during the fall.

18. The method of claim 14, wherein the negative pressure wound therapy device further comprises an electronic control circuitry configured to operate the negative pressure source, the method further comprising:

causing the electronic control circuitry to transition from a non-operational state to an operational state responsive to determining that the duration of the fall satisfies the duration threshold.

19. The method of claim 14, wherein the first indication comprises one or more of deactivating the negative pressure source or performing one or more tests of the negative pressure wound therapy device.

20. The method of claim 14, further comprising, at a second time:

based on the motion of the housing, detecting that the housing is tilted and providing a second indication responsive to detecting that the housing is tilted.

* * * * *